United States Patent
Shelton, IV et al.

(10) Patent No.: US 11,510,743 B2
(45) Date of Patent: Nov. 29, 2022

(54) COMMUNICATION CONTROL FOR A SURGEON CONTROLLED SECONDARY DISPLAY AND PRIMARY DISPLAY

(71) Applicant: Cilag GmbH International, Zug (CH)

(72) Inventors: Frederick E. Shelton, IV, New Vienna, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/062,507

(22) Filed: Oct. 2, 2020

(65) Prior Publication Data
US 2022/0104889 A1 Apr. 7, 2022

(51) Int. Cl.
*G06F 3/147* (2006.01)
*A61B 34/00* (2016.01)
(Continued)

(52) U.S. Cl.
CPC ............ *A61B 34/25* (2016.02); *A61B 17/072* (2013.01); *A61B 17/320092* (2013.01);
(Continued)

(58) Field of Classification Search
CPC ............ A61B 1/00013; A61B 1/00016; A61B 1/00045; A61B 1/00048; A61B 1/00009;
(Continued)

(56) References Cited

U.S. PATENT DOCUMENTS 9,011,427 B2 4/2015 Price et al.
9,345,481 B2 5/2016 Hall et al.
(Continued)

FOREIGN PATENT DOCUMENTS

CA 3089858 A1 8/2019
EP 2659852 A2 11/2013
(Continued)

OTHER PUBLICATIONS

U.S. Appl. No. 17/062,504, filed Oct. 2, 2020, Shelton, IV, et al.

*Primary Examiner* — Michael J Eurice
(74) *Attorney, Agent, or Firm* — Condo Roccia Koptiw LLP

(57) ABSTRACT

A tiered multi-display control scheme may provide various communication control options for a surgeon-controlled secondary display and primary operating room display. A powered surgical tool may be in operative communication with a local display and at least one main monitor within the operating room outside the sterile field for displaying multiple data and/or imaging sources. The local display may be interactable by the surgeon within the sterile field. The display outside the sterile field may show an image of an aspect of the laparoscopic scope and may contain superimposed other data streams from other devices besides the scope. The secondary display could be used to direct from its displayed content up onto the primary display or remove it from the display. The added or removed data streams may be originated from the secondary display, passed through the secondary display, or be networked with the secondary display.

20 Claims, 25 Drawing Sheets

(51) Int. Cl.
*G16H 40/63* (2018.01)
*A61B 17/072* (2006.01)
*A61B 17/32* (2006.01)
*A61B 18/14* (2006.01)
*G06F 3/14* (2006.01)
*A61B 34/37* (2016.01)
*A61B 5/021* (2006.01)
*A61B 17/00* (2006.01)
*A61B 18/00* (2006.01)

(52) U.S. Cl.
CPC ............ *A61B 18/14* (2013.01); *G06F 3/1423* (2013.01); *G16H 40/63* (2018.01); *A61B 5/021* (2013.01); *A61B 34/37* (2016.02); *A61B 2017/00039* (2013.01); *A61B 2017/00199* (2013.01); *A61B 2017/00221* (2013.01); *A61B 2017/00398* (2013.01); *A61B 2017/07235* (2013.01); *A61B 2017/07285* (2013.01); *A61B 2017/32007* (2017.08); *A61B 2017/320084* (2013.01); *A61B 2017/320095* (2017.08); *A61B 2017/320097* (2017.08); *A61B 2018/0063* (2013.01); *A61B 2018/00541* (2013.01); *A61B 2018/00565* (2013.01); *A61B 2018/00601* (2013.01); *A61B 2018/00994* (2013.01); *A61B 2034/252* (2016.02); *A61B 2034/256* (2016.02); *A61B 2034/258* (2016.02); *A61B 2218/002* (2013.01); *A61B 2218/007* (2013.01); *A61B 2218/008* (2013.01); *G06F 3/14* (2013.01)

(58) Field of Classification Search
CPC ....... A61B 5/021; A61B 6/464; A61B 17/072; A61B 17/320092; A61B 18/14; A61B 18/1445; A61B 34/25; A61B 34/30; A61B 34/37; A61B 90/361; A61B 90/37; A61B 2017/00115; A61B 2017/00199; A61B 2017/00221; A61B 2017/32007; A61B 2017/320084; A61B 2017/320095; A61B 2017/320097; A61B 2017/00039; A61B 2017/00398; A61B 2017/07235; A61B 2017/07285; A61B 2017/00473; A61B 2018/00541; A61B 2018/00565; A61B 2018/00601; A61B 2018/0063; A61B 2018/00994; A61B 2034/252; A61B 2034/256; A61B 2034/258; A61B 2050/105; A61B 2218/002; A61B 2218/007; A61B 2218/008; G01J 3/465; G01J 3/506; G02F 1/13336; G09F 13/0143; G06F 3/14; G06F 3/1423; G06F 3/1431; G06F 3/1438; G06F 3/1446; G09G 3/1423; G09G 3/2003; G09G 3/32; G09G 3/006; G09G 2300/026; G09G 2320/0242; G09G 2320/0276; G09G 2320/0666; G09G 2320/0673; G09G 2320/0693; G09G 2340/06; G09G 2360/145; G09G 2360/04; G16H 10/60; G16H 30/20; G16H 30/40; G16H 40/63; G16H 80/00; H04N 1/6052; H04N 9/3182; H04N 9/69; H04N 9/73

See application file for complete search history.

(56) References Cited

U.S. PATENT DOCUMENTS

| | | | |
|---|---|---|---|
| 10,881,399 B2 | 1/2021 | Shelton et al. | |
| 2005/0128184 A1* | 6/2005 | McGreevy | A61B 18/1206 345/156 |
| 2005/0134525 A1* | 6/2005 | Tanghe | G06F 3/1446 345/1.1 |
| 2011/0181394 A1* | 7/2011 | Blair | A61B 90/98 340/10.1 |
| 2012/0116365 A1* | 5/2012 | Price | A61B 90/40 606/1 |
| 2014/0066700 A1* | 3/2014 | Wilson | A61B 1/00045 600/102 |
| 2014/0263552 A1 | 9/2014 | Hall et al. | |
| 2015/0157416 A1* | 6/2015 | Andersson | A61B 34/10 606/102 |
| 2015/0223890 A1 | 8/2015 | Miller et al. | |
| 2016/0171330 A1* | 6/2016 | Mentese | G06V 10/25 348/170 |
| 2016/0332296 A1* | 11/2016 | Kurnianto | B29C 48/252 |
| 2017/0000575 A1* | 1/2017 | Griffiths | A61B 50/10 |
| 2017/0296213 A1 | 10/2017 | Swensgard et al. | |
| 2019/0117070 A1* | 4/2019 | Muhsin | G16H 40/67 |
| 2019/0125454 A1 | 5/2019 | Stokes et al. | |
| 2019/0200844 A1 | 7/2019 | Shelton et al. | |
| 2019/0200998 A1 | 7/2019 | Shelton, IV et al. | |
| 2019/0201044 A1 | 7/2019 | Shelton, IV et al. | |
| 2019/0201104 A1 | 7/2019 | Shelton et al. | |
| 2019/0201115 A1 | 7/2019 | Shelton et al. | |
| 2019/0201136 A1 | 7/2019 | Shelton et al. | |
| 2019/0201137 A1 | 7/2019 | Shelton et al. | |
| 2019/0206569 A1 | 7/2019 | Shelton et al. | |
| 2019/0388137 A1 | 12/2019 | Henrywood et al. | |
| 2020/0078078 A1 | 3/2020 | Henderson et al. | |
| 2020/0120308 A1* | 4/2020 | McMillan | H04N 7/15 |
| 2020/0214571 A1 | 7/2020 | Bradbury et al. | |
| 2020/0281790 A1* | 9/2020 | Augustine | A61M 16/009 |
| 2020/0350063 A1* | 11/2020 | Thornton | G06V 20/52 |
| 2021/0137581 A1* | 5/2021 | Reid | A61B 34/35 |

FOREIGN PATENT DOCUMENTS

| | | |
|---|---|---|
| EP | 3506299 A1 | 7/2019 |
| WO | WO 2019-130108 A1 | 7/2019 |

* cited by examiner

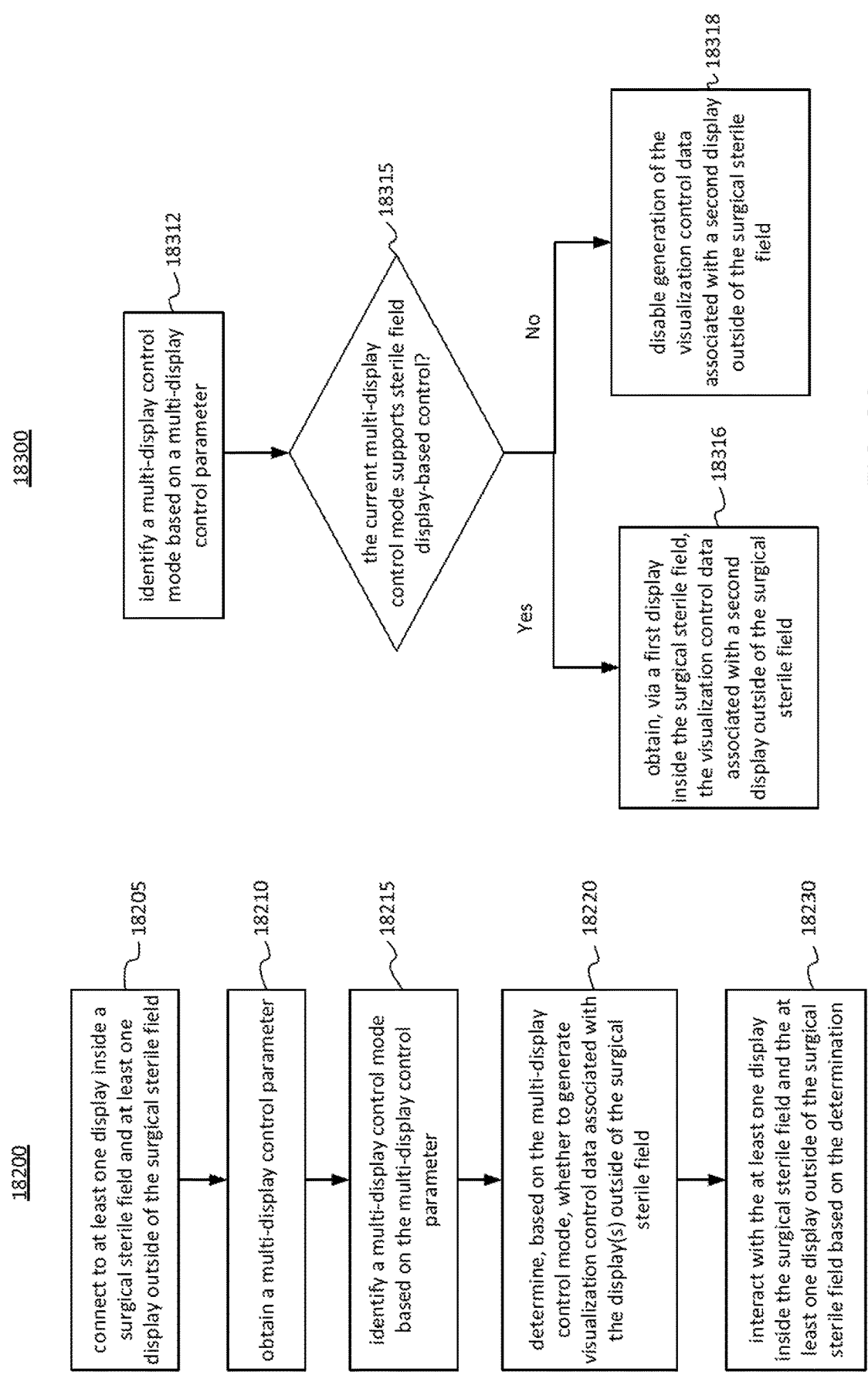

COMMUNICATION CONTROL FOR A SURGEON CONTROLLED SECONDARY DISPLAY AND PRIMARY DISPLAY

CROSS-REFERENCE TO RELATED APPLICATIONS

This application is related to the following, filed contemporaneously, the contents of each of which are incorporated by reference herein:

Ser. No. 17/062,504, titled METHOD FOR OPERATING TIERED OPERATION MODES IN A SURGICAL SYSTEM.

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

A powered surgical device may include a processor configured to obtain one or more multi-display control parameter(s) and identify a current multi-display control mode based on the multi-display control parameter(s). Based on the current multi-display control mode, whether to generate visualization control data associated with the display outside of the surgical sterile field may be determined. The powered surgical device may interact with the display inside the surgical sterile field and the display outside of the surgical sterile field based on the determination.

The multi-display(s) control parameter may include an indication from the surgical hub. The multi-display control parameter(s) may include a consumer-controlled parameter, such as a subscription level. The multi-display control parameter(s) may include available data bandwidth, power capacity and usage, processor and memory utilization, and/or internal or attached systems. The multi-display control parameter(s) may include an indication from a tiered system.

The powered surgical device may operate under various multi-display control modes such as one-way communication mode, sterile field display-based control mode, and/or remote aggregation analysis mode.

For example, when operating in an example one-way communication mode, the surgical device may receive content for displaying on the display inside the surgical sterile field and send the received content to the display. The content for displaying on the display inside the surgical sterile field may be received from a surgical hub.

For example, when operating in an example sterile field display-based control mode, the surgical instrument may obtain, via the display inside the surgical sterile field, the visualization control data associated with the display outside of the surgical sterile field. The surgical instrument may send the visualization control data associated with the display (e.g., to the surgical hub) for controlling the display outside of the surgical sterile field. When operating under a multi-display control mode does not support sterile field display-based control, the surgical instrument may disable generation of the visualization control data associated with the display outside of the surgical sterile field.

The surgical instrument may determine that the current multi-display control mode supports sterile field display-based control and may receive a user indication of changing the content on the display outside of the surgical sterile field. The surgical instrument may generate the visualization control data associated with the display outside of the surgical sterile field based on the received user indication, and send the visualization control data associated with the display outside of the surgical sterile field (e.g., to the surgical hub) for controlling the display outside of the surgical sterile field. The user indication of changing the content on the display outside of the surgical sterile field may be received via the display inside a surgical sterile field. The user indication may indicate projecting content associated with the display inside the surgical sterile field onto the display outside of the surgical sterile field, or removing the content associated with the display inside the surgical sterile field from the display outside of the surgical sterile field.

For example, when operating in an example remote aggregation analysis mode, surgical instrument may request aggregation analysis from a remote server (e.g., via the surgical hub). The surgical instrument may determine, based on the current multi-display control mode, whether to request aggregation analysis from a remote server (e.g., via the surgical hub). Based on a determination to request the aggregation analysis, an aggregation analysis request may be generated. An aggregation analysis response may be received and combined with surgical data generated based on the sensed surgical data for displaying on the display inside the surgical sterile field.

A surgical hub may include a communication array operably connected to a surgical instrument, a display inside a surgical sterile field and a display outside of the surgical sterile field. The surgical hub may include a processor configured to obtain a multi-display control parameter and identify a current multi-display control mode based on the multi-display control parameter. The surgical hub may interact at least one the display inside the surgical sterile field and at least one display outside of the surgical sterile field based on the current multi-display control mode. For example, the surgical hub may determine whether to receive visualization control data associated with a display outside of the surgical sterile field from a display inside the surgical sterile field based on the current multi-display control mode.

The surgical hub may operate under various multi-display control modes such as one-way communication mode, sterile field display-based control mode, and/or remote aggregation analysis mode.

Based on a determination that the current multi-display control mode supports sterile field display-based control, the surgical hub may receive the visualization control data associated with the display outside of the surgical sterile field, and may control the display outside of the surgical sterile field based on the received visualization control data associated with the display outside of the surgical sterile field.

The surgical hub may determine, based on the current multi-display control mode, whether to retrieve aggregation analysis from a remote server for displaying on the first display inside the surgical sterile field. Based on a determination that the current multi-display control mode supports remote aggregation, the surgical hub may generate an aggregation analysis request. The aggregation analysis request may be generated based on an indication from the display inside the sterile field. The surgical instrument may receive an aggregation analysis response, and may combine the received aggregation analysis response with surgical data received from the at least one instrument to generate content for displaying on first display inside the surgical sterile field.

BRIEF DESCRIPTION OF THE DRAWINGS

FIG. 19 shows example flow for operating under a multi-display control mode.

FIG. 20 shows an example flow for operating under tiered multi-display control mode(s).

DETAILED DESCRIPTION

Applicant of the present application owns the following U.S. patent applications, filed contemporaneously, each of which is herein incorporated by reference in its entirety:

U.S. patent application Ser. No. 15/940,671, entitled "SURGICAL HUB SPATIAL AWARENESS TO DETERMINE DEVICES IN OPERATING THEATER," filed Mar. 29, 2018;

U.S. Pat. No. 9,011,427, entitled SURGICAL INSTRUMENT WITH SAFETY GLASSES, issued on Apr. 21, 2015; and U.S. patent application Ser. No. 15/940,668 entitled "AGGREGATION AND REPORTING OF SURGICAL HUB DATA" filed on Mar. 29, 2018.

Figure 1:
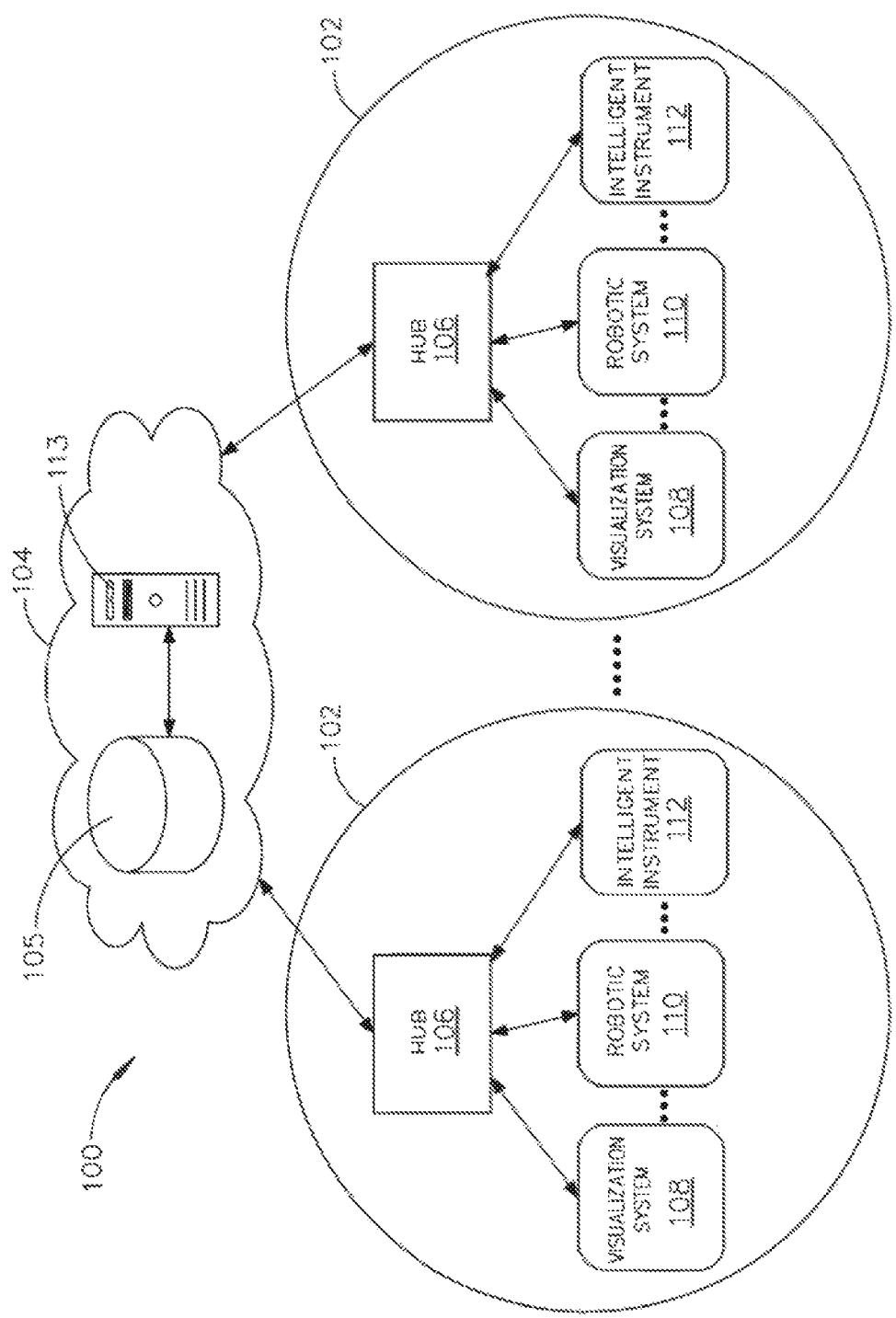
FIG. 1 is a block diagram of a computer-implemented interactive surgical system.

Referring to FIG. 1, a computer-implemented interactive surgical system 100 may include one or more surgical systems 102 and a cloud-based system (e.g., the cloud 104 that may include a remote server 113 coupled to a storage device 105). Each surgical system 102 may include at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P may be integers greater than or equal to one.

Figure 2:
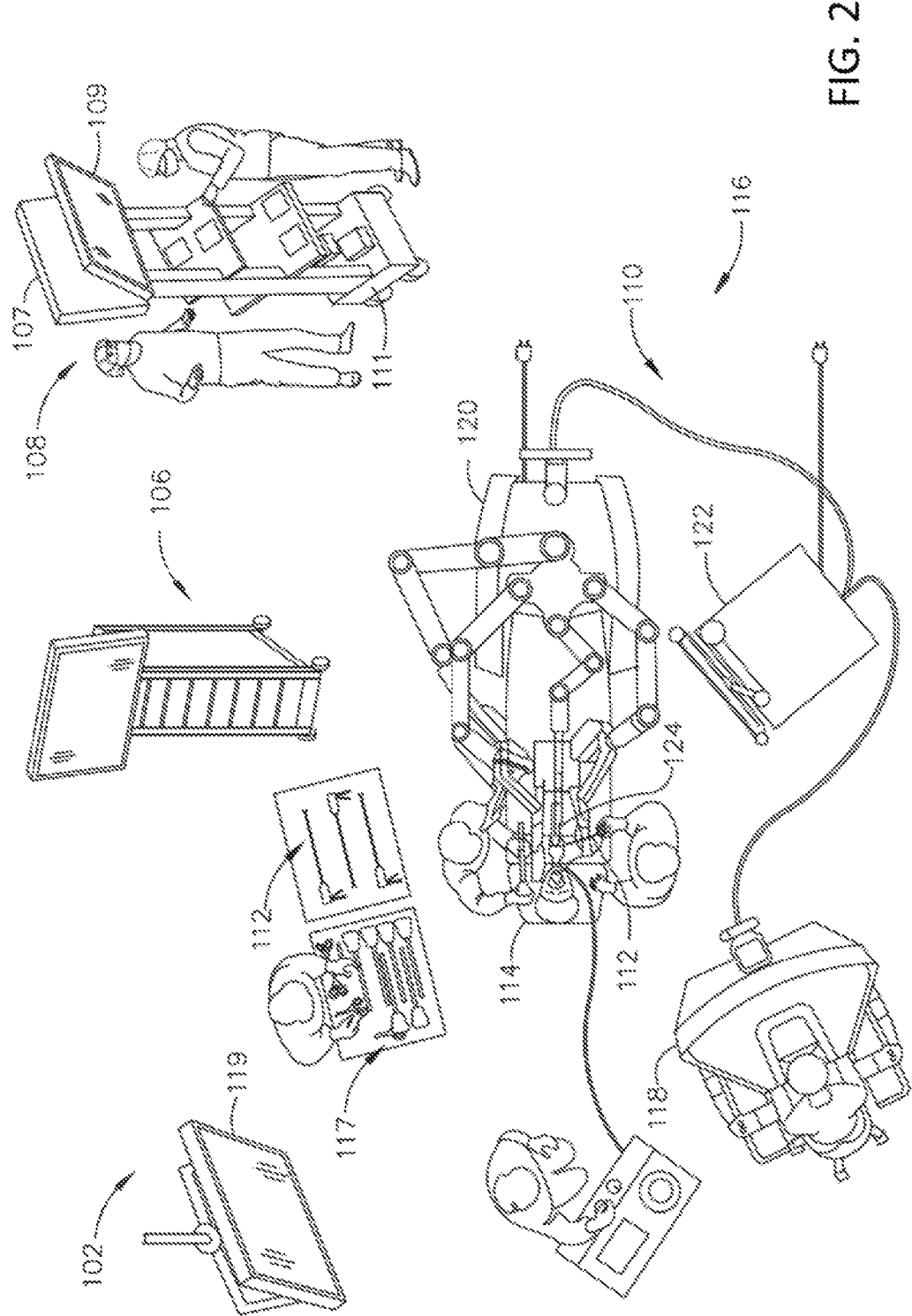
FIG. 2 shows an example surgical system being used to perform a surgical procedure in an operating room.

In various aspects, the visualization system 108 may include one or more imaging sensors, one or more image-processing units, one or more storage arrays, and one or more displays that are strategically arranged with respect to the sterile field, as illustrated in FIG. 2. In one aspect, the visualization system 108 may include an interface for HL7, PACS, and EMR. Various components of the visualization system 108 are described under the heading "Advanced Imaging Acquisition Module" in .US. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 may include a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 may also be configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 may also be configured to coordinate information flow to a display of the surgical instrument 112. For example, in U.S. Patent Application Publication No. US 2019-0200844 A1 (U.S. patent application Ser. No. 16/209, 385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 depicts an example of a surgical system 102 being used to perform a surgical procedure on a patient who is lying down on an operating table 114 in a surgical operating room 116. A robotic system 110 may be used in the surgical procedure as a part of the surgical system 102. The robotic system 110 may include a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud 104, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 124 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in .S. Patent Application Publication No. US 2019-0200844 A1 (U.S. patent application Ser. No. 16/209, 385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 3:
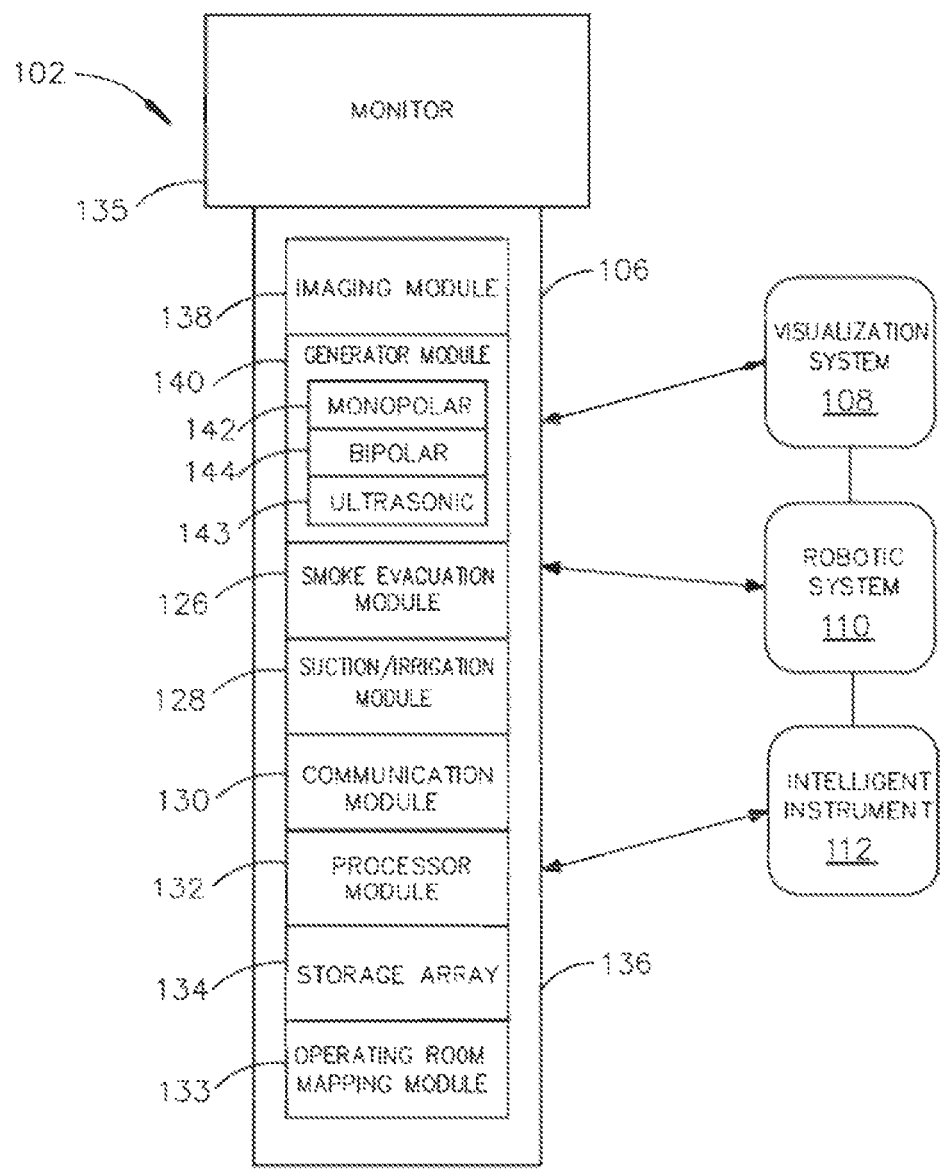
FIG. 3 shows an example surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, a storage array 134, and an operating-room mapping module 133. In certain aspects, as illustrated in FIG. 3, the hub 106 further includes a smoke evacuation module 126 and/or a suction/irrigation module 128. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines. Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line is a first fluid line and a second fluid line extends from the remote surgical site to a suction and irrigation module slidably received in the hub enclosure. In one aspect, the hub enclosure comprises a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 146. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

Figure 4:
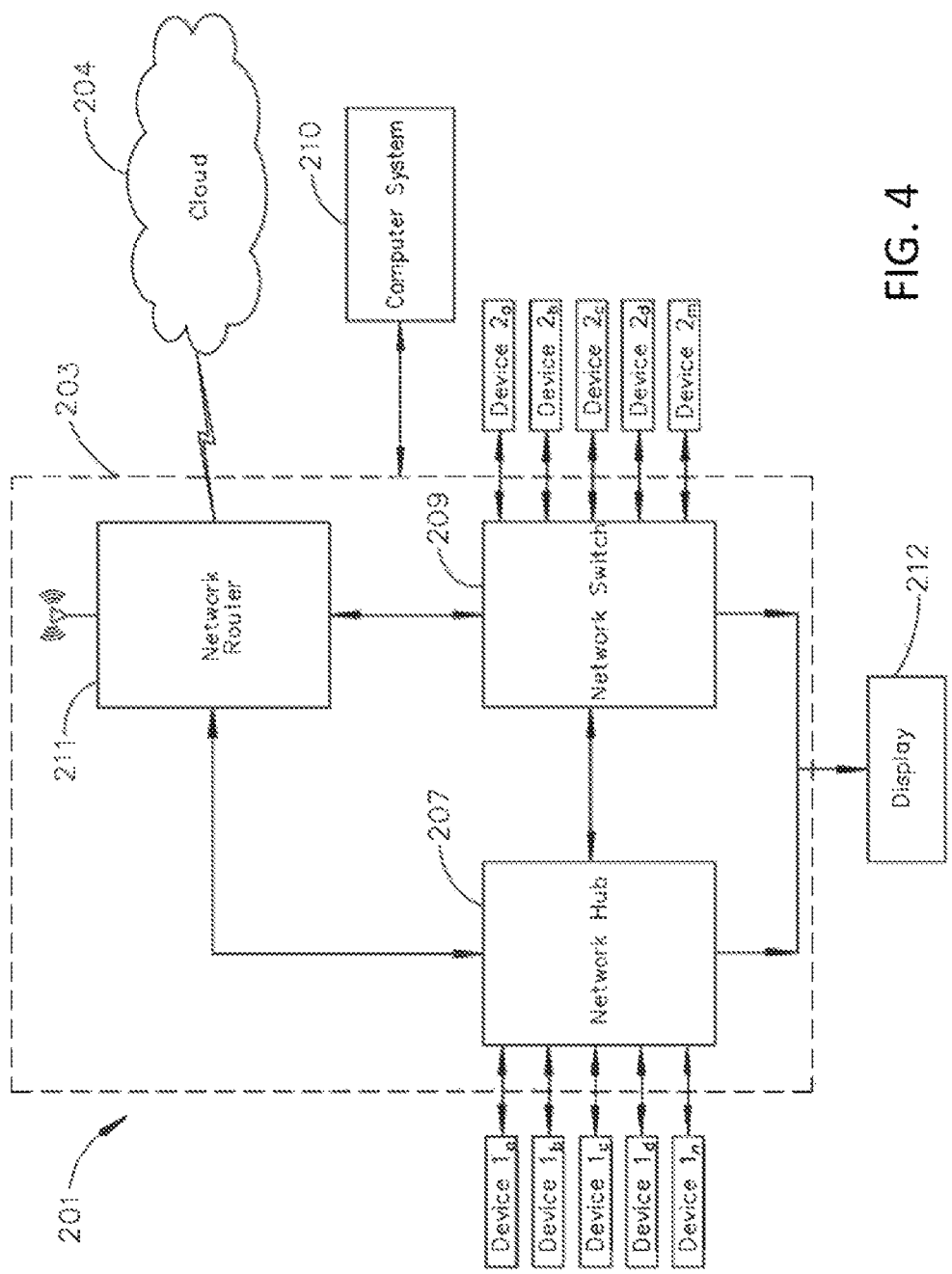
FIG. 4 illustrates a surgical data network having a communication hub configured to connect modular devices located in one or more operating theaters of a healthcare facility, or any room in a healthcare facility specially equipped for surgical operations, to the cloud, in accordance with at least one aspect of the present disclosure.

FIG. 4 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

The operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub may provide connectivity to the devices 1a-1n located in the same operating theater network. The network hub 207 may collect data in the form of packets and sends them to the router in half duplex mode. The network hub 207 may not store any media access control/Internet Protocol (MAC/IP) to transfer the device data. Only one of the devices 1a-1n can send data at a time through the network hub 207. The network hub 207 may not have routing tables or intelligence regarding where to send information and broadcasts all network data across each connection and to a remote server 213 (FIG. 4) over the cloud 204. The network hub 207 can detect basic network errors such as collisions, but having all information broadcast to multiple ports can be a security risk and cause bottlenecks.

The operating theater devices 2a-2m may be connected to a network switch 209 over a wired channel or a wireless channel. The network switch 209 works in the data link layer of the OSI model. The network switch 209 may be a multicast device for connecting the devices 2a-2m located in the same operating theater to the network. The network switch 209 may send data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 may be coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 may send data in the form of packets to the cloud 204 and works in full duplex mode. Multiple devices can send data at the same time. The network router 211 uses IP addresses to transfer data.

In an example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANS). The operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and may handle a data type known as frames. Frames may carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 can be generally easy to install, configure, and maintain, making it a good option for networking the operating theater devices 1a-1n/2a-2m.

Figure 5:
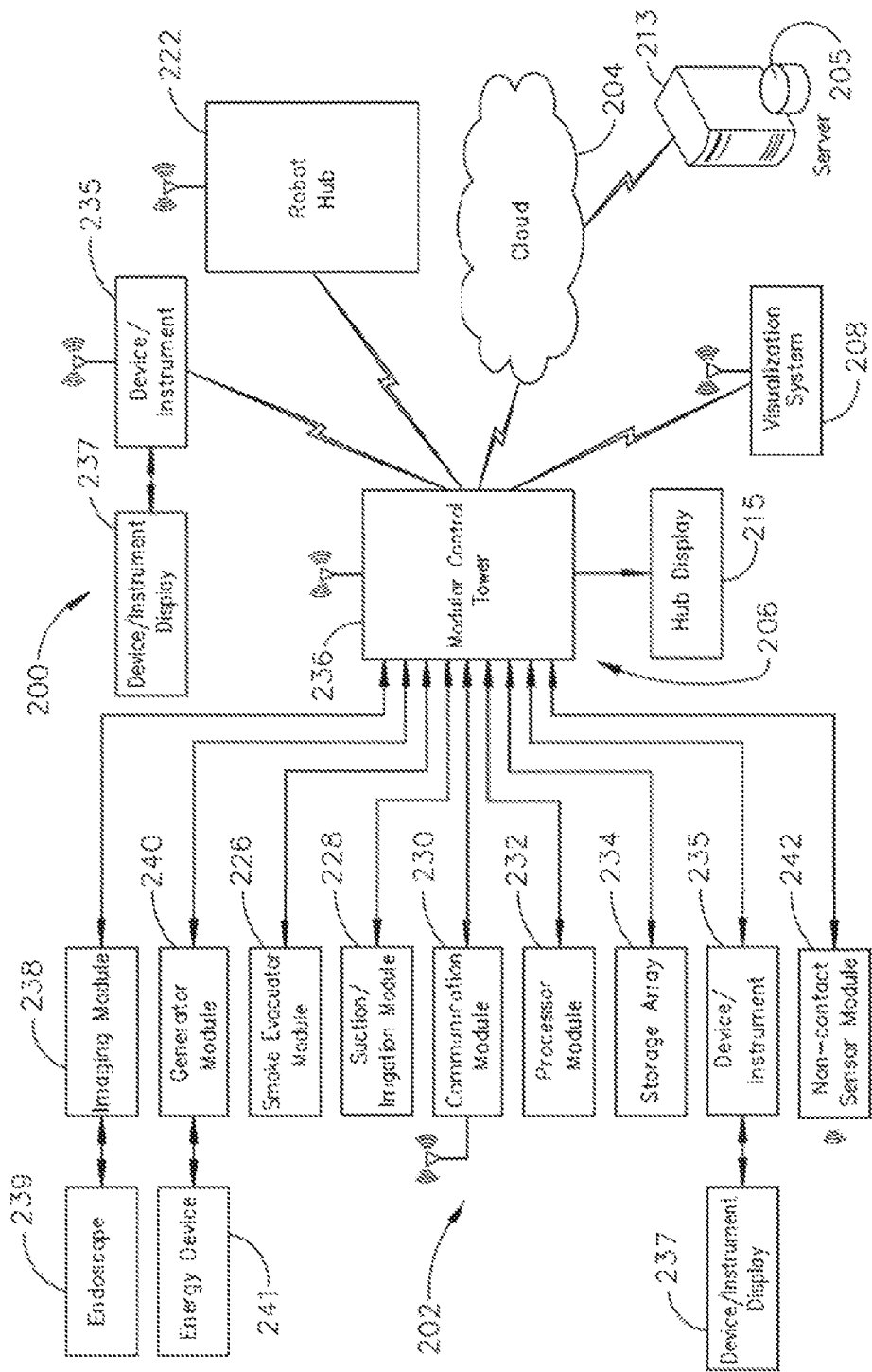
FIG. 5 illustrates an example computer-implemented interactive surgical system.
Figure 6:
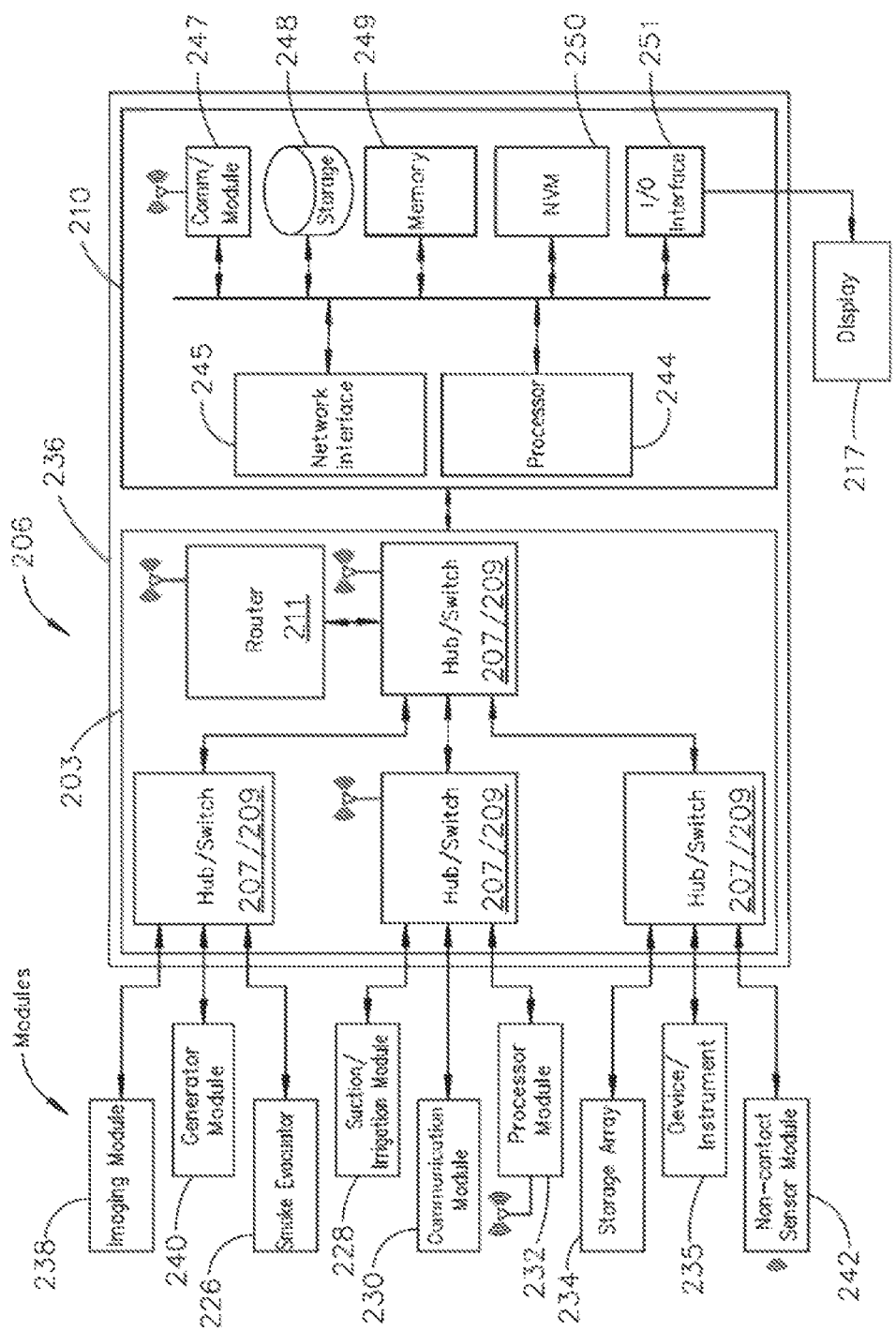
FIG. 6 illustrates an example surgical hub comprising a plurality of modules coupled to the modular control tower.

FIG. 5 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 6, the modular control tower 236 comprises a modular communication hub 203 coupled to a computer system 210.

As illustrated in the example of FIG. 5, the modular control tower 236 may be coupled to an imaging module 238 that may be coupled to an endoscope 239, a generator module 240 that may be coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices may be coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 6 illustrates a surgical hub 206 comprising a plurality of modules coupled to the modular control tower 236. The modular control tower 236 may comprise a modular communication hub 203, e.g., a network connectivity device, and a computer system 210 to provide local processing, visualization, and imaging, for example. As shown in FIG. 6, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 6, each of the network hubs/switches in the modular communication hub 203 may include three downstream ports and one upstream port. The upstream network hub/switch may be connected to a processor to provide a communication connection to the cloud computing resources and a local display 217. Communication to the cloud 204 may be made either through a wired or a wireless communication channel.

The surgical hub 206 may employ a non-contact sensor module 242 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in .S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 may comprise a processor 244 and a network interface 245. The processor 244 can be coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 210 through input device(s) coupled to the I/O interface 251. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5 and the like. WAN technologies may include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 6, the imaging module 238 and/or visualization system 208, and/or the processor module 232 of FIGS. 5-6, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system, it can also be external to the computer system 210. The hardware/software necessary for connection to the network interface may include, for illustrative purposes only, internal and external technologies such as modems, including regular telephone-grade modems, cable modems, and DSL modems, ISDN adapters, and Ethernet cards.

Figure 7:
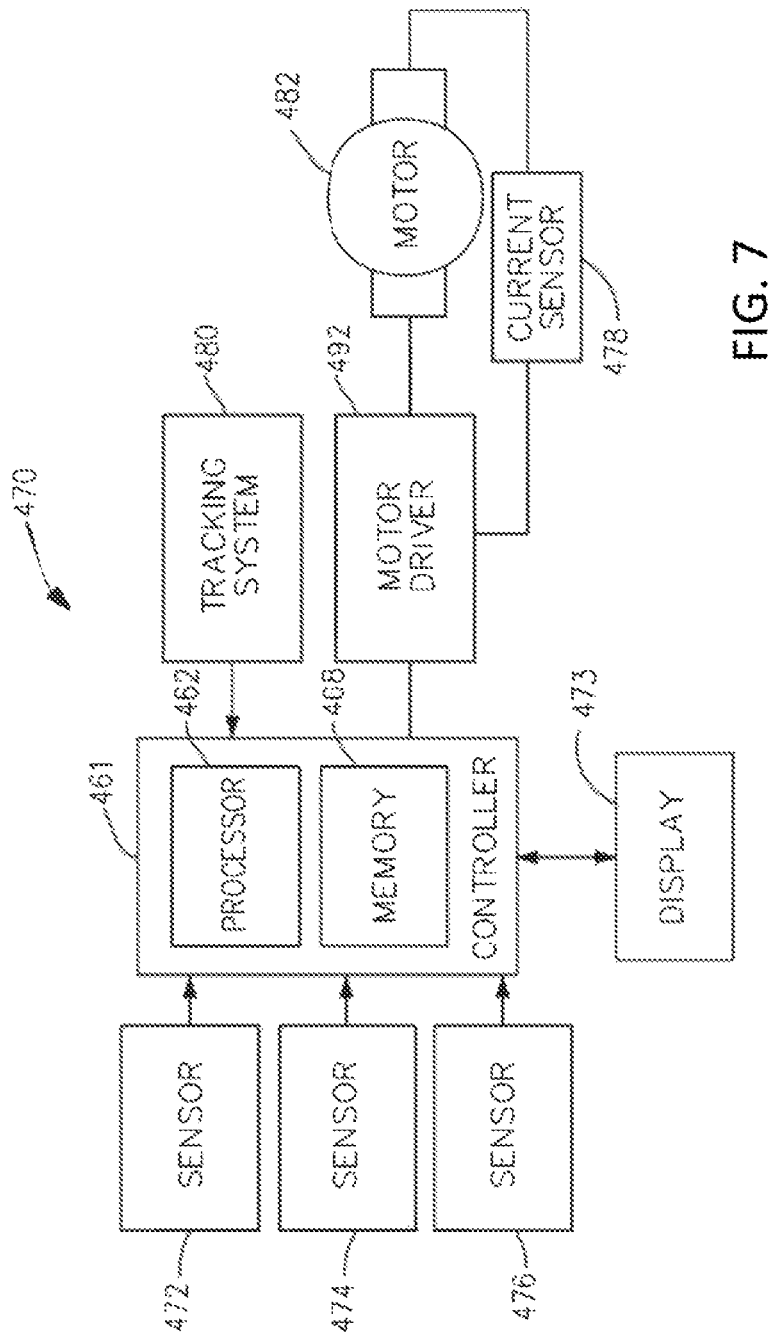
FIG. 7 shows an example surgical instrument or tool.

FIG. 7 illustrates a logic diagram of a control system 470 of a surgical instrument or tool in accordance with one or more aspects of the present disclosure. The system 470 may comprise a control circuit. The control circuit may include a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 may be configured to determine the position of the longitudinally movable displacement member. The position information may be provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 may display a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 may include a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

In some examples, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In some examples, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 may be a full-bridge controller for use with external N-channel power metal-oxide semiconductor field-effect transistors (MOSFETs) specifically designed for inductive loads, such as brush DC motors. The driver 492 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the lowside FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 may comprise a controlled motor drive circuit arrangement comprising a position sensor 472 according to one aspect of this disclosure. The position sensor 472 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 472 may be equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches may be fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system may comprise a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 may be a low-voltage and low-power component and includes four Hall-effect elements in an area of the position sensor 472 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bitshift, and table lookup operations. The angle position, alarm bits, and magnetic field information may be transmitted over a standard serial communication interface, such as a serial peripheral interface (SPI) interface, to the microcontroller 461. The position sensor 472 may provide 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertial, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force may be converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 474, such as, for example, a micro-strain gauge, that can be configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain can be converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub 203 as shown in FIGS. 5 and 6.

Figure 8:
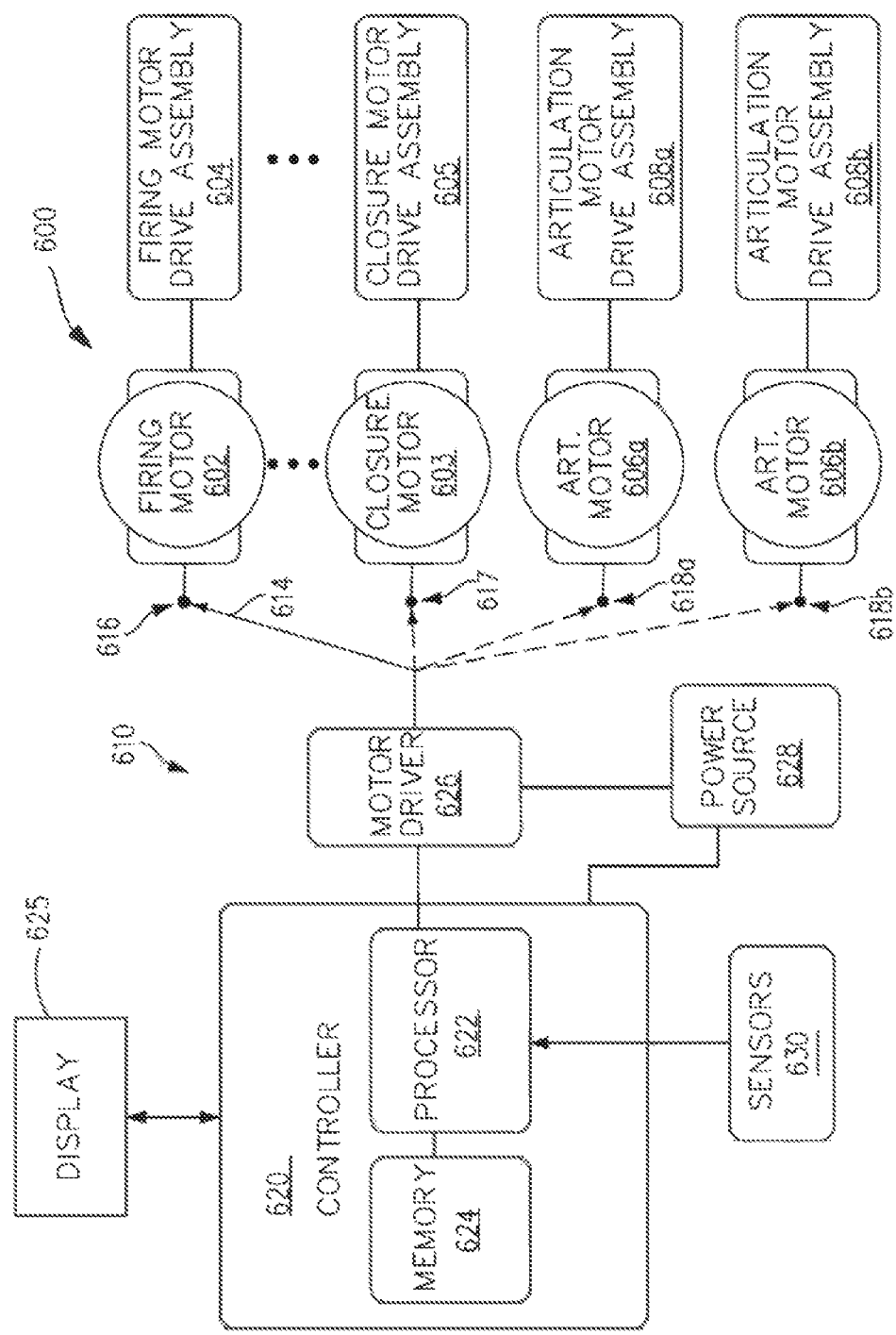
FIG. 8 illustrates an example surgical instrument or tool having motors that can be activated to perform various functions.

FIG. 8 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described herein, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 8, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 8, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described herein.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor can be a multipurpose, programmable device that accepts digital data as input, processes it according to instructions stored in its memory, and provides results as output. It can be an example of sequential digital logic, as it may have internal memory. Processors may operate on numbers and symbols represented in the binary numeral system.

The processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

The memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

One or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 9:
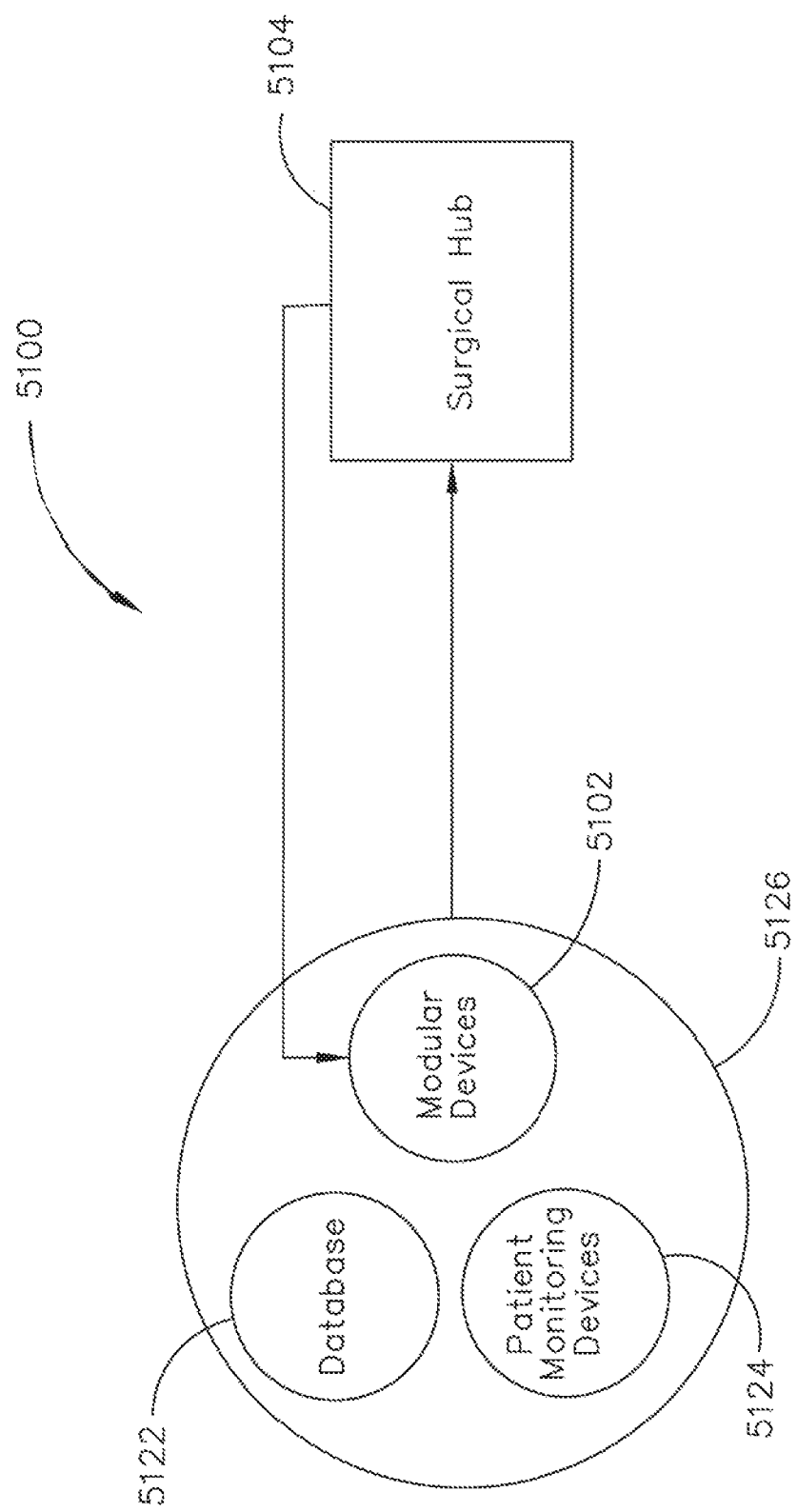
FIG. 9 is a diagram of an example situationally aware surgical system.

FIG. 9 illustrates a diagram of a situationally aware surgical system 5100, in accordance with at least one aspect of the present disclosure. In some exemplifications, the data sources 5126 may include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In an exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In an exemplification, the situational awareness system can include a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in an exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use a soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can be configured to compare the list of items for the procedure and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In some exemplifications, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In some exemplifications, the surgical hub 5104 can be configured to provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Figure 10:
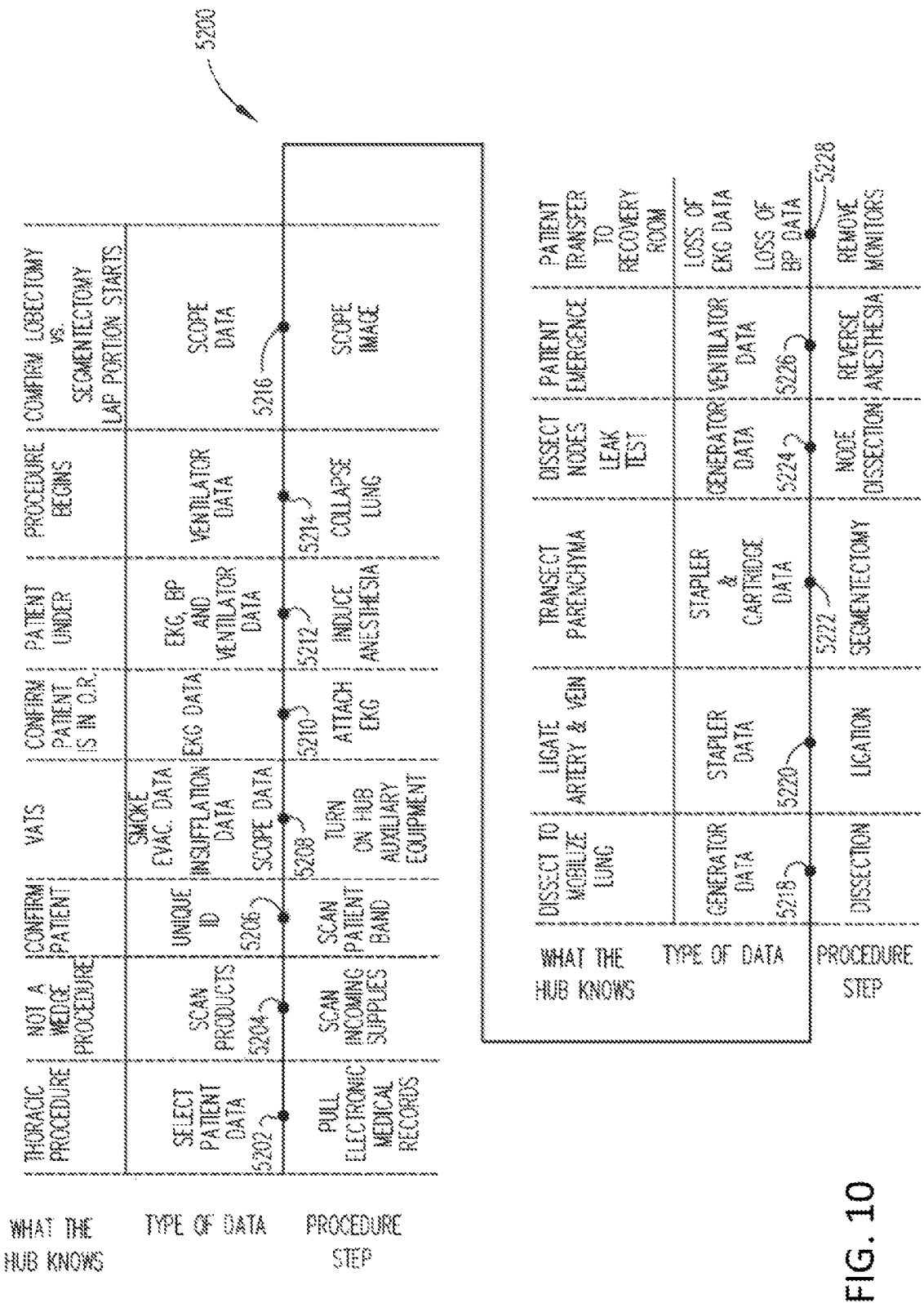
FIG. 10 illustrates an example timeline of an illustrative surgical procedure and the inferences that the surgical hub can make from the data detected at each step in the surgical procedure.

FIG. 10 illustrates a timeline 5200 of an illustrative surgical procedure and the contextual information that a surgical hub 5104 can derive from the data received from the data sources 5126 at each step in the surgical procedure. In the following description of the timeline 5200 illustrated in FIG. 9, reference should also be made to FIG. 9. The timeline 5200 may depict the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 may receive data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 can be able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described herein.

As the first step 5202 in this illustrative procedure, the hospital staff members may retrieve the patient's EMR from the hospital's EMR database. Based on select patient data in the EMR, the surgical hub 5104 determines that the procedure to be performed is a thoracic procedure. Second 5204, the staff members may scan the incoming medical supplies for the procedure. The surgical hub 5104 cross-references the scanned supplies with a list of supplies that can be utilized in various types of procedures and confirms that the mix of supplies corresponds to a thoracic procedure. Further, the surgical hub 5104 may also be able to determine that the procedure is not a wedge procedure (because the incoming supplies either lack certain supplies that are necessary for a thoracic wedge procedure or do not otherwise correspond to a thoracic wedge procedure). Third 5206, the medical personnel may scan the patient band via a scanner 5128 that is communicably connected to the surgical hub 5104. The surgical hub 5104 can then confirm the patient's identity based on the scanned data. Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that may be located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 may determine that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing. Fifth 5210, the staff members attach the EKG electrodes and other patient monitoring devices 5124 to the patient. The EKG electrodes and other patient monitoring devices 5124 may pair with the surgical hub 5104. As the surgical hub 5104 begins receiving data from the patient monitoring devices 5124, the surgical hub 5104 may confirm that the patient is in the operating theater, as described in the process 5207, for example. Sixth 5212, the medical personnel may induce anesthesia in the patient. The surgical hub 5104 can infer that the patient is under anesthesia based on data from the modular devices 5102 and/or patient monitoring devices 5124, including EKG data, blood pressure data, ventilator data, or combinations thereof. for example. Upon completion of the sixth step 5212, the pre-operative portion of the lung segmentectomy procedure is completed and the operative portion begins.

Seventh 5214, the patient's lung that is being operated on may be collapsed (while ventilation is switched to the contralateral lung). The surgical hub 5104 can infer from the ventilator data that the patient's lung has been collapsed, for example. The surgical hub 5104 can infer that the operative portion of the procedure has commenced as it can compare the detection of the patient's lung collapsing to the expected steps of the procedure (which can be accessed or retrieved previously) and thereby determine that collapsing the lung can be the first operative step in this particular procedure. Eighth 5216, the medical imaging device 5108 (e.g., a scope) may be inserted and video from the medical imaging device may be initiated. The surgical hub 5104 may receive the medical imaging device data (i.e., video or image data) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized. For example, one technique for performing a VATS lobectomy may place the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. An example technique for performing a VATS lobectomy may utilize a single medical imaging device. An example technique for performing a VATS segmentectomy utilizes multiple cameras. An example technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team may begin the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step. Tenth 5220, the surgical team may proceed to the ligation step of the procedure. The surgical hub 5104 can infer that the surgeon is ligating arteries and veins because it may receive data from the surgical stapling and cutting instrument indicating that the instrument is being fired. Similar to the prior step, the surgical hub 5104 can derive this inference by cross-referencing the receipt of data from the surgical stapling and cutting instrument with the retrieved steps in the process. Eleventh 5222, the segmentectomy portion of the procedure can be performed. The surgical hub 5104 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 5104 to infer that the segmentectomy portion of the procedure is being performed. Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (e.g., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure may begin.

Thirteenth 5226, the patient's anesthesia can be reversed. The surgical hub 5104 can infer that the patient is emerging from the anesthesia based on the ventilator data (i.e., the patient's breathing rate begins increasing), for example. Lastly, the fourteenth step 5228 may be that the medical personnel remove the various patient monitoring devices 5124 from the patient. The surgical hub 5104 can thus infer that the patient is being transferred to a recovery room when the hub loses EKG, BP, and other data from the patient monitoring devices 5124. As can be seen from the description of this illustrative procedure, the surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step 5202 of the timeline 5200 depicted in FIG. 10, the patient data can also be utilized by a situationally aware surgical hub 5104 to generate control adjustments for the paired modular devices 5102.

Figure 11:
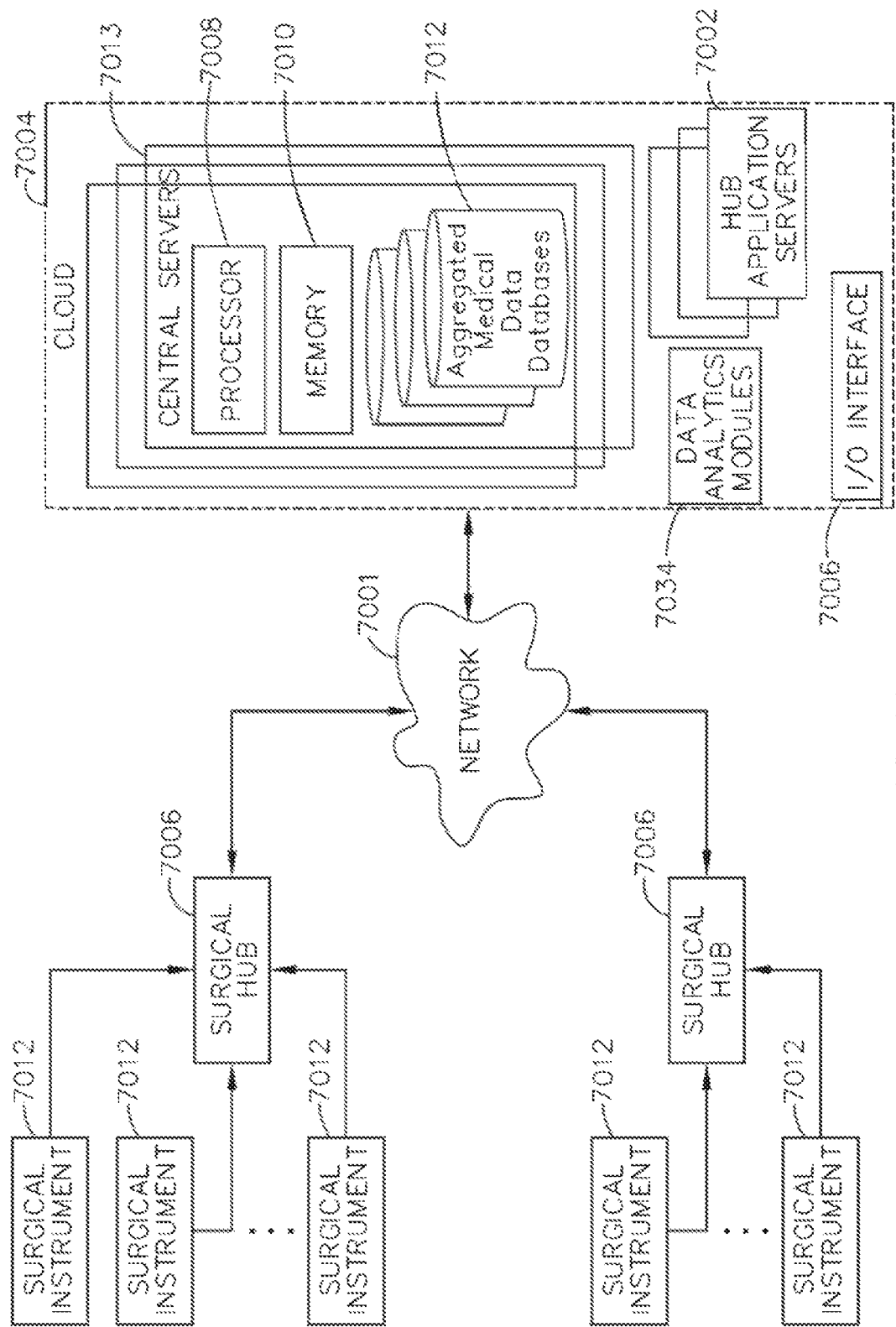
FIG. 11 is a block diagram of the computer-implemented interactive surgical system.

FIG. 11 is a block diagram of the computer-implemented interactive surgical system, in accordance with at least one aspect of the present disclosure. In one aspect, the computer-implemented interactive surgical system may be configured to monitor and analyze data related to the operation of various surgical systems that include surgical hubs, surgical instruments, robotic devices and operating theaters or healthcare facilities. The computer-implemented interactive surgical system may comprise a cloud-based analytics system. Although the cloud-based analytics system may be described as a surgical system, it may not be necessarily limited as such and could be a cloud-based medical system generally. As illustrated in FIG. 11, the cloud-based analytics system may comprise a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 may be communicatively coupled to one or more surgical instruments 7012. The hubs 7006 may also be communicatively coupled to the cloud 7004 of the computer-implemented interactive surgical system via the network 7001. The cloud 7004 may be a remote centralized source of hardware and software for storing, manipulating, and communicating data generated based on the operation of various surgical systems. As shown in FIG. 11, access to the cloud 7004 may be achieved via the network 7001, which may be the Internet or some other suitable computer network. Surgical hubs 7006 that may be coupled to the cloud 7004 can be considered the client side of the cloud computing system (i.e., cloud-based analytics system). Surgical instruments 7012 may be paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 11, the cloud 7004 comprises central servers 7013 (may be same or similar to remote server 7013), hub application servers 7002, data analytics modules 7034, and an input/output ("I/O") interface 7006. The central servers 7013 of the cloud 7004 collectively administer the cloud computing system, which includes monitoring requests by client surgical hubs 7006 and managing the processing capacity of the cloud 7004 for executing the requests. Each of the central servers 7013 may comprise one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also may comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7012 of the cloud 7004. In particular, the cloud 7004 may advantageously perform data analysis and operations on the aggregated data to yield insights and/or perform functions that individual hubs 7006 could not achieve on their own. To this end, as shown in FIG. 11, the cloud 7004 and the surgical hubs 7006 are communicatively coupled to transmit and receive information. The I/O interface 7006 is connected to the plurality of surgical hubs 7006 via the network 7001. In this way, the I/O interface 7006 can be configured to transfer information between the surgical hubs 7006 and the aggregated medical data databases 7011. Accordingly, the I/O interface 7006 may facilitate read/write operations of the cloud-based analytics system. Such read/write operations may be executed in response to requests from hubs 7006. These requests could be transmitted to the hubs 7006 through the hub applications. The I/O interface 7006 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 may be configured to host and supply shared capabilities to software applications (e.g., hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 12.

The particular cloud computing system configuration described in the present disclosure may be specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch-controlled user interfaces such that clinicians may control aspects of interaction between the surgical instruments 7012 and the cloud 7004. Other suitable user interfaces for control such as auditory controlled user interfaces can also be used.

Figure 12:
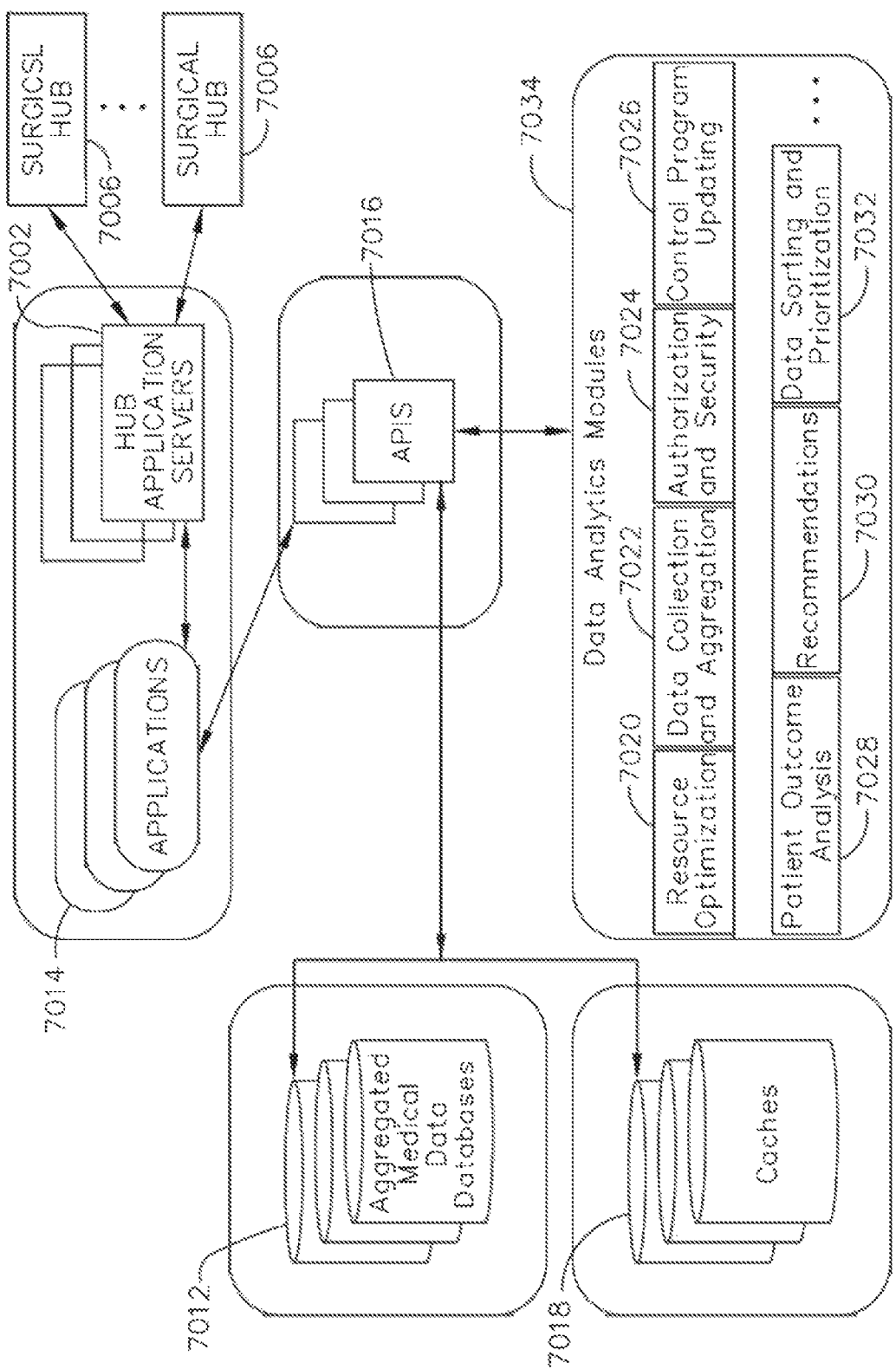
FIG. 12 illustrates the functional architecture of an example computer-implemented interactive surgical system.

FIG. 12 is a block diagram which illustrates the functional architecture of the computer-implemented interactive surgical system, in accordance with at least one aspect of the present disclosure. The cloud-based analytics system may include a plurality of data analytics modules 7034 that may be executed by the processors 7008 of the cloud 7004 for providing data analytic solutions to problems specifically arising in the medical field. As shown in FIG. 12, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 may define the set of protocols and routines corresponding to the hub applications 7014. Additionally, the APIs 7016 may manage the storing and retrieval of data into and from the aggregated medical databases 7012 for the operations of the applications 7014. The caches 7018 may also store data (e.g., temporarily) and may be coupled to the APIs 7016 for more efficient retrieval of data used by the applications 7014. The data analytics modules 7034 in FIG. 12 may include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules may be used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities.

For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently. The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that may be transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004. Furthermore, for security purposes, the cloud could maintain a database of hubs 7006, instruments 7012, and other devices that may comprise a "black list" of prohibited devices. In particular, a surgical hubs 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally, or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash-based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local region of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described herein to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g., a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been comprised, for example.

Additional example details for the various functions described are provided in the ensuing descriptions below. Each of the various descriptions may utilize the cloud architecture as described in FIGS. 11 and 12 as one example of hardware and software implementation.

Figure 13:
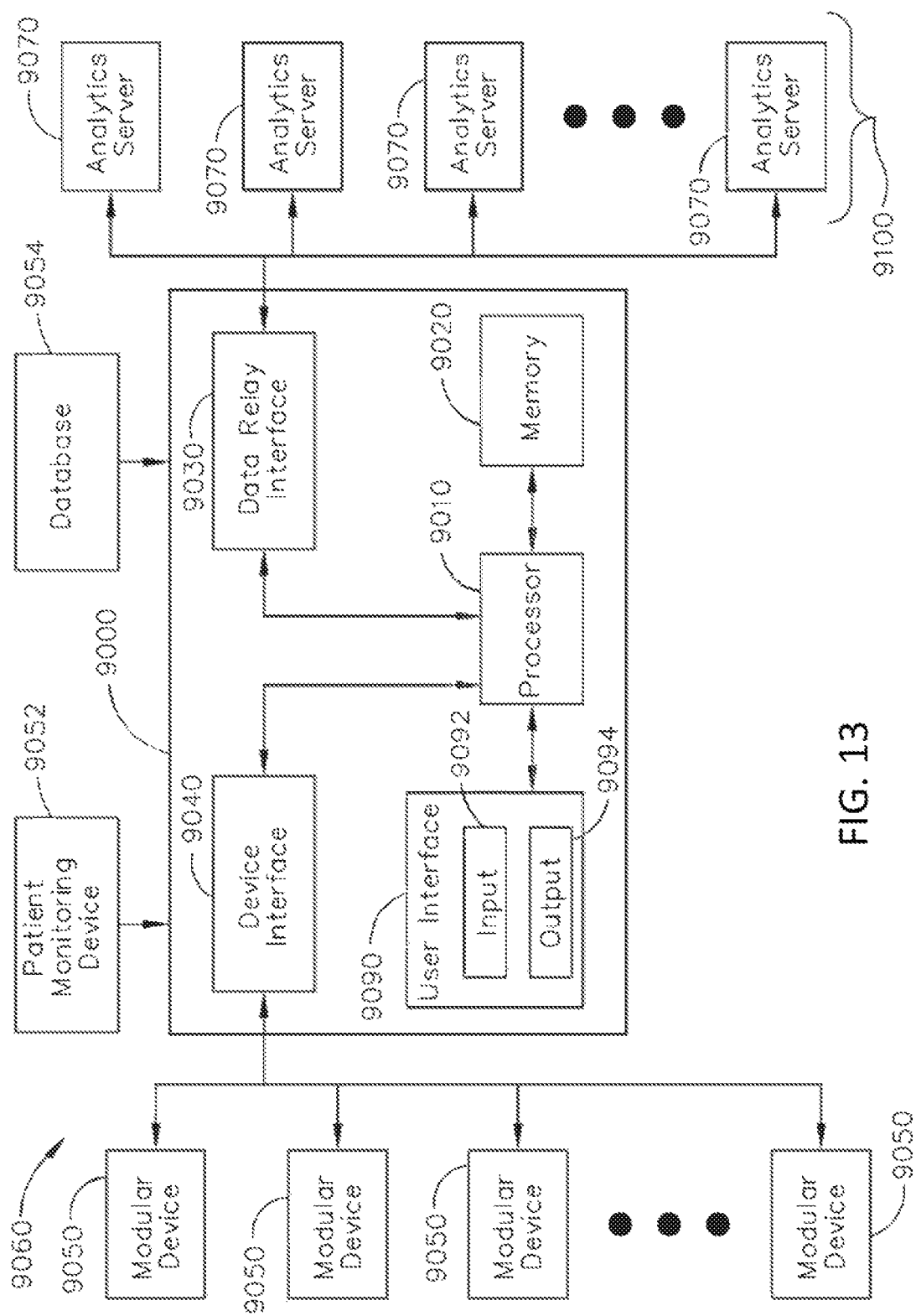
FIG. 13 illustrates an example computer-implemented interactive surgical system that is configured to adaptively generate control program updates for modular devices.

FIG. 13 illustrates a block diagram of a computer-implemented adaptive surgical system 9060 that is configured to adaptively generate control program updates for modular devices 9050, in accordance with at least one aspect of the present disclosure. In some exemplifications, the surgical system may include a surgical hub 9000, multiple modular devices 9050 communicably coupled to the surgical hub 9000, and an analytics system 9100 communicably coupled to the surgical hub 9000. Although a single surgical hub 9000 may be depicted, it should be noted that the surgical system 9060 can include any number of surgical hubs 9000, which can be connected to form a network of surgical hubs 9000 that are communicably coupled to the analytics system 9010. In some exemplifications, the surgical hub 9000 may include a processor 9010 coupled to a memory 9020 for executing instructions stored thereon and a data relay interface 9030 through which data is transmitted to the analytics system 9100. In some exemplifications, the surgical hub 9000 further may include a user interface 9090 having an input device 9092 (e.g., a capacitive touchscreen or a keyboard) for receiving inputs from a user and an output device 9094 (e.g., a display screen) for providing outputs to a user. Outputs can include data from a query input by the user, suggestions for products or mixes of products to use in a given procedure, and/or instructions for actions to be carried out before, during, or after surgical procedures. The surgical hub 9000 further may include an interface 9040 for communicably coupling the modular devices 9050 to the surgical hub 9000. In one aspect, the interface 9040 may include a transceiver that is communicably connectable to the modular device 9050 via a wireless communication protocol. The modular devices 9050 can include, for example, surgical stapling and cutting instruments, electrosurgical instruments, ultrasonic instruments, insufflators, respirators, and display screens. In some exemplifications, the surgical hub 9000 can further be communicably coupled to one or more patient monitoring devices 9052, such as EKG monitors or BP monitors. In some exemplifications, the surgical hub 9000 can further be communicably coupled to one or more databases 9054 or external computer systems, such as an EMR database of the medical facility at which the surgical hub 9000 is located.

When the modular devices 9050 are connected to the surgical hub 9000, the surgical hub 9000 can sense or receive perioperative data from the modular devices 9050 and then associate the received perioperative data with surgical procedural outcome data. The perioperative data may indicate how the modular devices 9050 were controlled during the course of a surgical procedure. The procedural outcome data includes data associated with a result from the surgical procedure (or a step thereof), which can include whether the surgical procedure (or a step thereof) had a positive or negative outcome. For example, the outcome data could include whether a patient suffered from postoperative complications from a particular procedure or whether there was leakage (e.g., bleeding or air leakage) at a particular staple or incision line. The surgical hub 9000 can obtain the surgical procedural outcome data by receiving the data from an external source (e.g., from an EMR database 9054), by directly detecting the outcome (e.g., via one of the connected modular devices 9050), or inferring the occurrence of the outcomes through a situational awareness system. For example, data regarding postoperative complications could be retrieved from an EMR database 9054 and data regarding staple or incision line leakages could be directly detected or inferred by a situational awareness system. The surgical procedural outcome data can be inferred by a situational awareness system from data received from a variety of data sources, including the modular devices 9050 themselves, the patient monitoring device 9052, and the databases 9054 to which the surgical hub 9000 is connected.

The surgical hub 9000 can transmit the associated modular device 9050 data and outcome data to the analytics system 9100 for processing thereon. By transmitting both the perioperative data indicating how the modular devices 9050 are controlled and the procedural outcome data, the analytics system 9100 can correlate the different manners of controlling the modular devices 9050 with surgical outcomes for the particular procedure type. In some exemplifications, the analytics system 9100 may include a network of analytics servers 9070 that are configured to receive data from the surgical hubs 9000. Each of the analytics servers 9070 can include a memory and a processor coupled to the memory that is executing instructions stored thereon to analyze the received data. In some exemplifications, the analytics servers 9070 may be connected in a distributed computing architecture and/or utilize a cloud computing architecture. Based on this paired data, the analytics system 9100 can then learn optimal or preferred operating parameters for the various types of modular devices 9050, generate adjustments to the control programs of the modular devices 9050 in the field, and then transmit (or "push") updates to the modular devices' 9050 control programs.

Additional detail regarding the computer-implemented interactive surgical system 9060, including the surgical hub 9000 and various modular devices 9050 connectable thereto, are described in connection with FIGS. 5-6.

Figure 14:
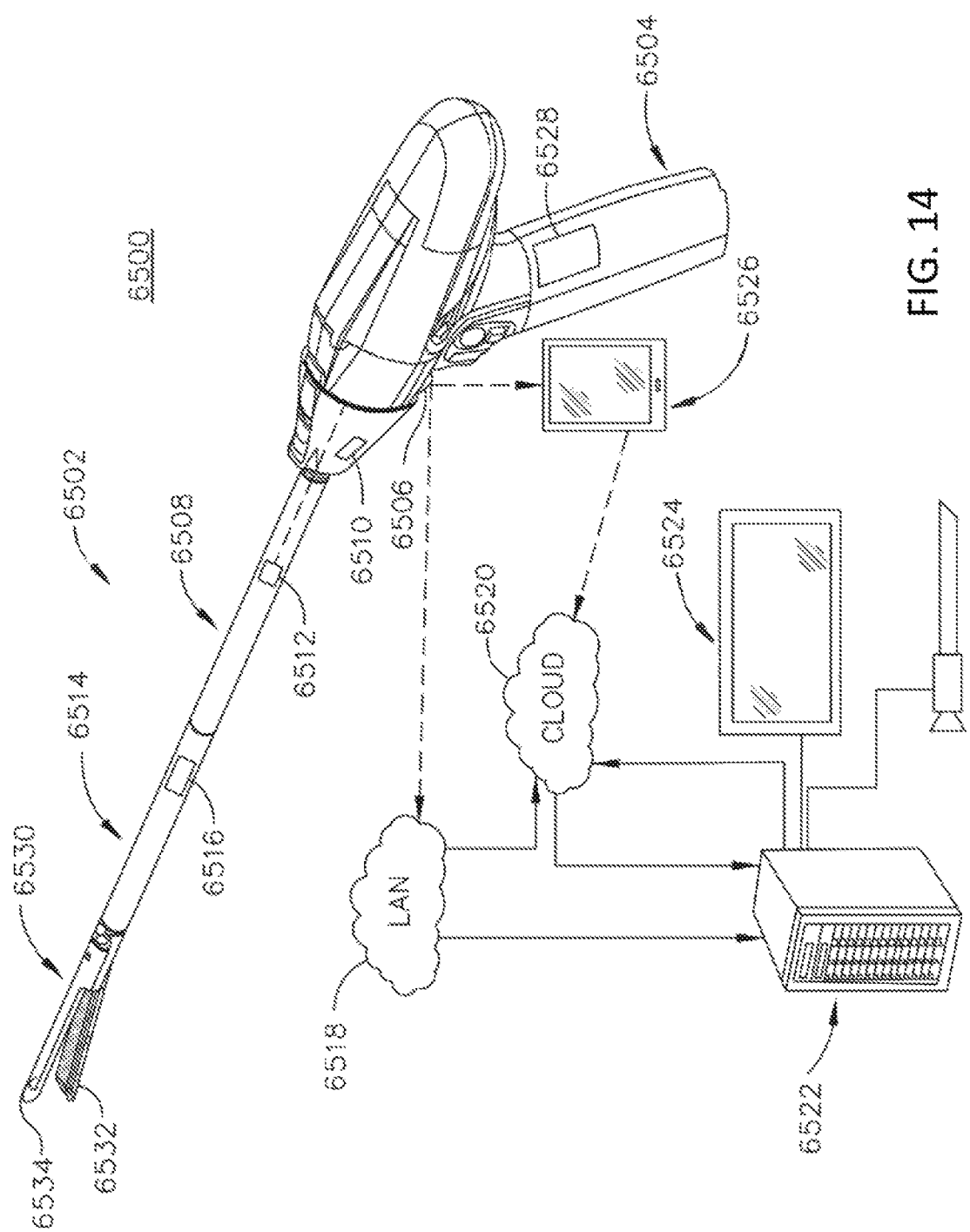
FIG. 14 illustrates an example surgical system that includes a handle having a controller and a motor, an adapter releasably coupled to the handle, and a loading unit releasably coupled to the adapter.

FIG. 14 provides a surgical system 6500 in accordance with the present disclosure and may include a surgical instrument 6502 that can be in communication with a console 6522 or a portable device 6526 through a local area network 6518 or a cloud network 6520 via a wired or wireless connection. In various aspects, the console 6522 and the portable device 6526 may be any suitable computing device. The surgical instrument 6502 may include a handle 6504, an adapter 6508, and a loading unit 6514. The adapter 6508 releasably couples to the handle 6504 and the loading unit 6514 releasably couples to the adapter 6508 such that the adapter 6508 transmits a force from a drive shaft to the loading unit 6514. The adapter 6508 or the loading unit 6514 may include a force gauge (not explicitly shown) disposed therein to measure a force exerted on the loading unit 6514. The loading unit 6514 may include an end effector 6530 having a first jaw 6532 and a second jaw 6534. The loading unit 6514 may be an in-situ loaded or multi-firing loading unit (MFLU) that allows a clinician to fire a plurality of fasteners multiple times without requiring the loading unit 6514 to be removed from a surgical site to reload the loading unit 6514.

The first and second jaws 6532, 6534 may be configured to clamp tissue therebetween, fire fasteners through the clamped tissue, and sever the clamped tissue. The first jaw 6532 may be configured to fire at least one fastener a plurality of times, or may be configured to include a replaceable multi-fire fastener cartridge including a plurality of fasteners (e.g., staples, clips, etc.) that may be fired more than one time prior to being replaced. The second jaw 6534 may include an anvil that deforms or otherwise secures the fasteners about tissue as the fasteners are ejected from the multi-fire fastener cartridge.

The handle 6504 may include a motor that is coupled to the drive shaft to affect rotation of the drive shaft. The handle 6504 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 6504 may be in communication with a controller 6528 of the handle 6504 to selectively activate the motor to affect rotation of the drive shafts. The controller 6528 may be disposed within the handle 6504 and is configured to receive input from the control interface and adapter data from the adapter 6508 or loading unit data from the loading unit 6514. The controller 6528 may analyze the input from the control interface and the data received from the adapter 6508 and/or loading unit 6514 to selectively activate the motor. The handle 6504 may also include a display that is viewable by a clinician during use of the handle 6504. The display may be configured to display portions of the adapter or loading unit data before, during, or after firing of the instrument 6502.

The adapter 6508 may include an adapter identification device 6510 disposed therein and the loading unit 6514 includes a loading unit identification device 6516 disposed therein. The adapter identification device 6510 may be in communication with the controller 6528, and the loading unit identification device 6516 may be in communication with the controller 6528. It will be appreciated that the loading unit identification device 6516 may be in communication with the adapter identification device 6510, which relays or passes communication from the loading unit identification device 6516 to the controller 6528.

The adapter 6508 may also include a plurality of sensors 6512 (one shown) disposed thereabout to detect various conditions of the adapter 6508 or of the environment (e.g., if the adapter 6508 is connected to a loading unit, if the adapter 6508 is connected to a handle, if the drive shafts are rotating, the torque of the drive shafts, the strain of the drive shafts, the temperature within the adapter 6508, a number of firings of the adapter 6508, a peak force of the adapter 6508 during firing, a total amount of force applied to the adapter 6508, a peak retraction force of the adapter 6508, a number of pauses of the adapter 6508 during firing, etc.). The plurality of sensors 6512 may provide an input to the adapter identification device 6510 in the form of data signals. The data signals of the plurality of sensors 6512 may be stored within, or be used to update the adapter data stored within, the adapter identification device 6510. The data signals of the plurality of sensors 6512 may be analog or digital. The plurality of sensors 6512 may include a force gauge to measure a force exerted on the loading unit 6514 during firing.

The handle 6504 and the adapter 6508 can be configured to interconnect the adapter identification device 6510 and the loading unit identification device 6516 with the controller 6528 via an electrical interface. The electrical interface may be a direct electrical interface (i.e., include electrical contacts that engage one another to transmit energy and signals therebetween). Additionally or alternatively, the electrical interface may be a non-contact electrical interface to wirelessly transmit energy and signals therebetween (e.g., inductively transfer). It is also contemplated that the adapter identification device 6510 and the controller 6528 may be in wireless communication with one another via a wireless connection separate from the electrical interface.

The handle 6504 may include a transmitter 6506 that is configured to transmit instrument data from the controller 6528 to other components of the system 6500 (e.g., the LAN 6518, the cloud 6520, the console 6522, or the portable device 6526). The transmitter 6506 also may receive data (e.g., cartridge data, loading unit data, or adapter data) from the other components of the system 6500. For example, the controller 6528 may transmit instrument data including a serial number of an attached adapter (e.g., adapter 6508)

attached to the handle 6504, a serial number of a loading unit (e.g., loading unit 6514) attached to the adapter, and a serial number of a multi-fire fastener cartridge (e.g., multi-fire fastener cartridge), loaded into the loading unit, to the console 6528. Thereafter, the console 6522 may transmit data (e.g., cartridge data, loading unit data, or adapter data) associated with the attached cartridge, loading unit, and adapter, respectively, back to the controller 6528. The controller 6528 can display messages on the local instrument display or transmit the message, via transmitter 6506, to the console 6522 or the portable device 6526 to display the message on the display 6524 or portable device screen, respectively.

Figures 15A, 15B:
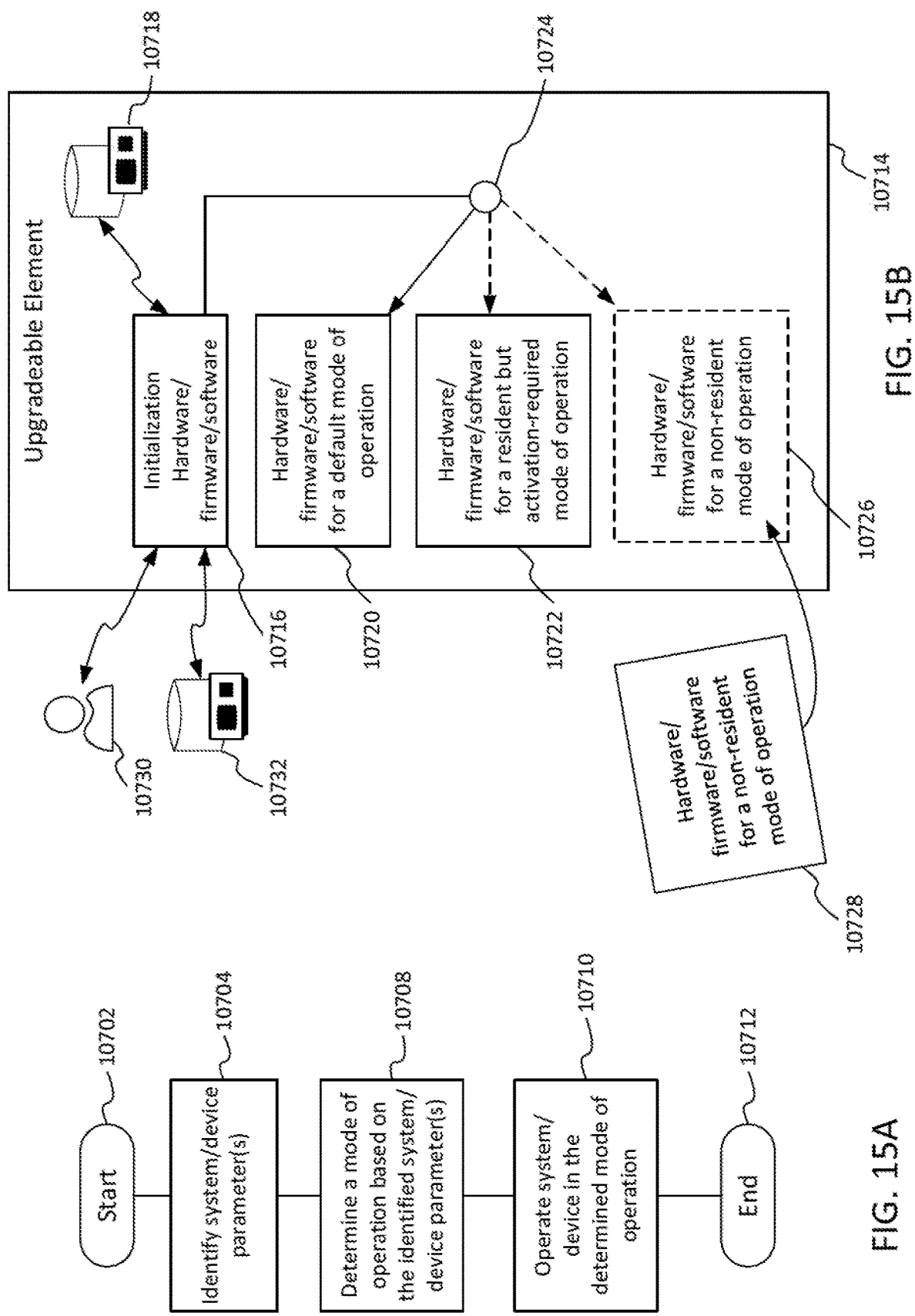
FIG. 15A illustrates an example flow for determining a mode of operation and operating in the determined mode.
FIG. 15B illustrates an example flow for changing a mode of operation.

FIG. 15A illustrates an example flow for determining a mode of operation and operating in the determined mode. The computer-implemented interactive surgical system and/or components and/or subsystems of the computer-implemented interactive surgical system may be configured to be updated. Such updates may include the inclusions of features and benefits that were not available to the user before the update. These updates may be established by any method of hardware, firmware, and software updates suitable for introducing the feature to the user. For example, replaceable/swappable (e.g., hot swappable) hardware components, flashable firmware devices, and updatable software systems may be used to update computer-implemented interactive surgical system and/or components and/or subsystems of the computer-implemented interactive surgical system.

The updates may be conditioned on any suitable criterion or set of criteria. For example, an update may be conditioned on one or more hardware capabilities of the system, such as processing capability, bandwidth, resolution, and the like. For example, the update may be conditioned on one or more software aspects, such as a purchase of certain software code. For example, the update may be conditioned on a purchased service tier. The service tier may represent a feature and/or a set of features the user is entitled to use in connection with the computer-implemented interactive surgical system. The service tier may be determined by a license code, an e-commerce server authentication interaction, a hardware key, a username/password combination, a biometric authentication interaction, a public/private key exchange interaction, or the like.

At 10704, a system/device parameter may be identified. The system/device parameter may be any element or set of elements on which an update in conditioned. For example, the computer-implemented interactive surgical system may detect a certain bandwidth of communication between a modular device and a surgical hub. For example, the computer-implemented interactive surgical system may detect an indication of the purchase of certain service tier.

At 10708, a mode of operation may be determined based on the identified system/device parameter. This determination may be made by a process that maps system/device parameters to modes of operation. The process may be a manual and/or an automated process. The process may be the result of local computation and/or remote computation. For example, a client/server interaction may be used to determine the mode of operation based on the on the identified system/device parameter. For example, local software and/or locally embedded firmware may be used to determine the mode of operation based on the identified system/device parameter. For example, a hardware key, such as a secure microprocessor for example, may be used to determine the mode of operation based on the identified system/device parameter.

At 10710, operation may proceed in accordance with the determined mode of operation. For example, a system or device may proceed to operate in a default mode of operation. For example, a system or device may proceed to operate in an alternate mode of operation. The mode of operation may be directed by control hardware, firmware, and/or software already resident in the system or device. The mode of operation may be directed by control hardware, firmware, and/or software newly installed/updated.

FIG. 15B illustrates an example functional block diagram for changing a mode of operation. An upgradeable element 10714 may include an initialization component 10716. The initialization component 10716 may include any hardware, firmware, and/or software suitable determining a mode of operation. For example, the initialization component 10716 may be portion of a system or device start-up procedure. The initialization component 10716 may engage in an interaction to determine a mode of operation for the upgradeable element 10714. For example, the initialization component 10716 may interact with a user 10730, an external resource 10732, and/or a local resource 10718 for example. For example, the initialization component 10716 may receive a licensing key from the user 10730 to determine a mode of operation. The initialization component 10716 may query an external resource 10732, such as a server for example, with a serial number of the upgradable device 10714 to determine a mode of operation. For example, the initialization component 10716 may query a local resource 10718, such as a local query to determine an amount of available bandwidth and/or a local query of a hardware key for example, to determine a mode of operation.

The upgradeable element 10714 may include one or more operation components 10720, 10722, 10726, 10728 and an operational pointer 10724. The initialization component 10716 may direct the operational pointer 10724 to direct the operation of the upgradable element 10741 to the operation component 10720, 10722, 10726, 10728 that corresponds with the determined mode of operation. The initialization component 10716 may direct the operational pointer 10724 to direct the operation of the upgradable element to a default operation component 10720. For example, the default operation component 10720 may be selected on the condition of no other alternate mode of operation being determined. For example, the default operation component 10720 may be selected on the condition of a failure of the initialization component and/or interaction failure. The initialization component 10716 may direct the operational pointer 10724 to direct the operation of the upgradable element 10714 to a resident operation component 10722. For example, certain features may be resident in the upgradable component 10714 but require activation to be put into operation. The initialization component 10716 may direct the operational pointer 10724 to direct the operation of the upgradable element 10714 to install a new operation component 10728 and/or a new installed operation component 10726. For example, new software and/or firmware may be downloaded. The new software and or firmware may contain code to enable the features represented by the selected mode of operation. For example, a new hardware component may be installed to enable the selected mode of operation.

As described herein, a tiered multi-display control scheme may provide various communication control options for a healthcare professional-controlled secondary display and primary operating room display. For example, a powered surgical tool may be in operative communication with a local display and at least one main monitor within the operating room outside the sterile field for displaying multiple data and/or imaging sources. The local display may be interactable by the surgeon within the sterile field. The display outside the sterile field, such as a main external display may show an image of an aspect of the laparoscopic scope and may contain superimposed other data streams from other devices besides the scope. The secondary display could be used to direct from its displayed content up onto the primary display or remove it from the display. The added or removed data streams may be originated from the secondary display, passed through the secondary display, or be networked with the secondary display. The secondary display could be part of a surgical instrument such as the powered surgical tool. The secondary display may be a dedicated display system controlled by a healthcare personnel within the sterile field.

FIG. 19 shows an example flow 18200 for operating under tiered multi-display control mode(s). As shown in FIG. 19, at 18205, a device such as a powered surgical device or a surgical hub may be connected to one or more display(s) inside the surgical sterile field and one or more display(s) outside of the surgical sterile field. The powered surgical device may be or may include surgical instruments 112 shown in FIG. 1, the surgical instrument 600 shown in FIG. 8, or the modular devices 5102 shown in FIG. 9, for example. The powered surgical device may include a communication array operably connected to display(s) inside and outside the surgical sterile field.

The display outside of the sterile field may be or may include the non-sterile display 107 or 109 as shown in FIG. 2. For example, the display inside a surgical sterile field may be or may include a secondary display such as a local display or a display on a surgical instrument. The display inside a surgical sterile field may be a secondary display. A healthcare personnel may control the secondary display. The primary display(s) and secondary display(s) may have numerous communication levels of operation with the primary hub system. Examples of primary display(s) and secondary display(s) can be found in more detail in U.S. patent application Ser. No. 15/940,671, tided SURGICAL HUB SPATIAL AWARENESS TO DETERMINE DEVICES IN OPERATING THEATER, which was filed on Mar. 29, 2018, which is herein incorporated by reference in its entirety.

Figure 16:
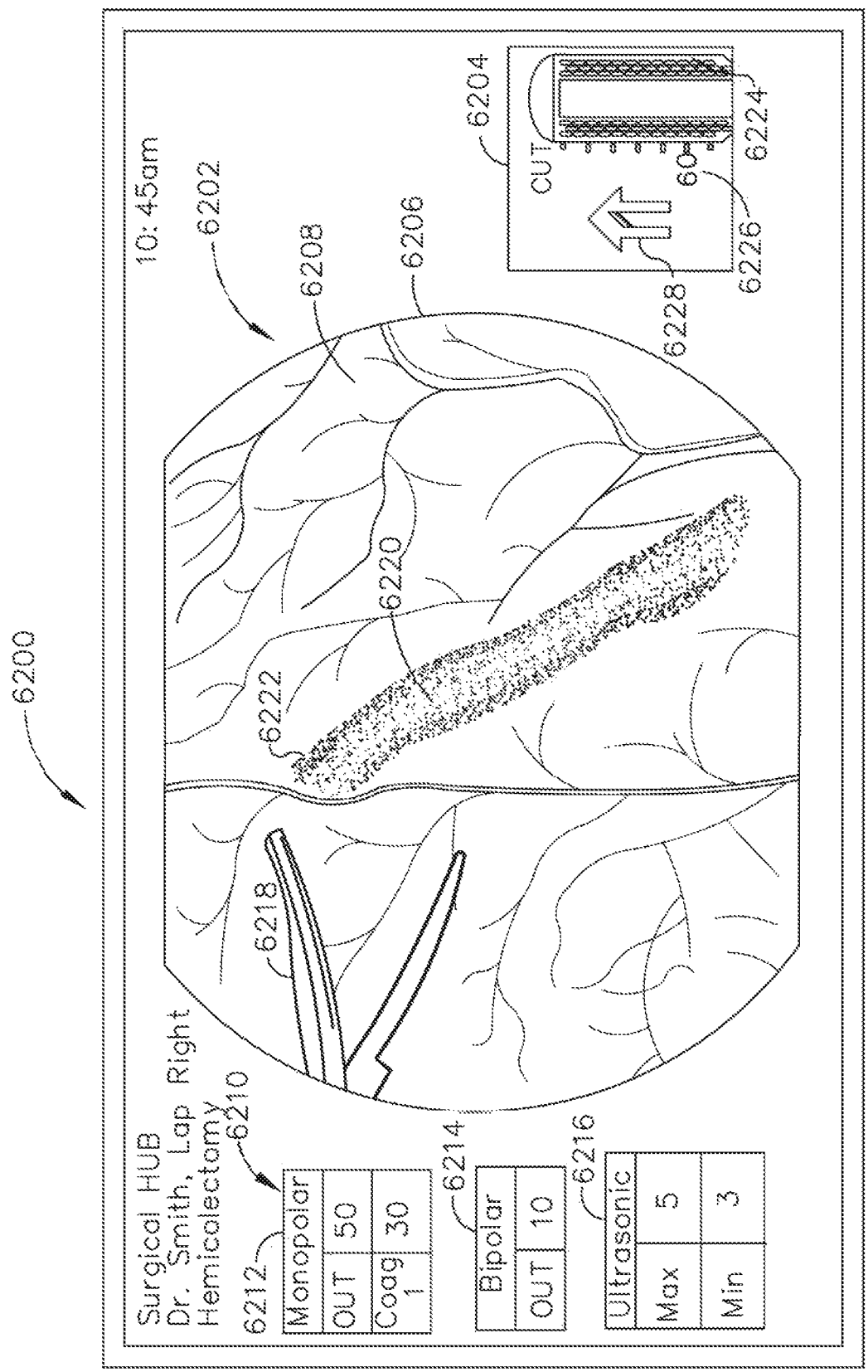
FIG. 16 illustrates a primary display of the surgical hub comprising a global and local display.

FIG. 16 illustrates an example primary display 6200 associate with the surgical hub 206 comprising a global display window 6202 and a local instrument display window 6204, according to one aspect of the present disclosure. With continued reference to FIGS. 1-11 to show interaction with an interactive surgical system 100 environment including a surgical hub 106, 206 and FIGS. 12-14 for surgical hub connected instruments together, the local instrument display 6204 behavior may be displayed when the instrument 235 senses the connectable presence of a global display window 6202 through the surgical hub 206. The global display window 6202 may show a field of view 6206 of a surgical site 6208, as viewed through a medical imaging device such as, for example, a laparoscope/endoscope 219 coupled to an imaging module 238, at the center of the surgical hub display 215, referred to herein also as a monitor, for example. The end effector 6218 portion of the connected instrument 235 may be shown in the field of view 6206 of the surgical site 6208 in the global display window 6202. The images shown on the display 237 located on an instrument 235 coupled to the surgical hub 206 is shown, or mirrored, on the local instrument display window 6204 located in the lower right corner of the monitor 6200 as shown in FIG. 16, for example.

During operation, relevant instrument and information and menus may be displayed on the display 237 located on the instrument 235 until the instrument 235 senses a connection of the instrument 235 to the surgical hub 206 at which point all or some sub-set of the information presented on the instrument display 237 may be displayed (e.g., only) on the local instrument display window 6204 portion of the surgical hub display 6200 through the surgical hub 206. The information displayed on the local instrument display window 6204 may be mirrored on the display 237 located on the instrument 235 or may be no longer accessible on the instrument display 237 detonated screen. This technique frees up the instrument 235 to show different information or to show larger font information on the surgical hub display 6200.

The primary display 6200 may provide perioperative visualization of the surgical site 6208. Advanced imaging may identify and visually highlight 6222 critical structures such as the ureter 6220 (or nerves, etc.) and may track instrument proximity displays 6210 and shown on the left side of the display 6200. In the illustrated example, the instrument proximity displays 6210 may show instrument specific settings. For example, the top instrument proximity display 6212 may show settings for a monopolar instrument, the middle instrument proximity display 6214 may show settings for a bipolar instrument, and the bottom instrument proximity display 6212 may show settings for an ultrasonic instrument.

Secondary displays may include independent secondary displays and/or dedicated local displays that can be linked to the surgical hub 206 to provide an interaction portal via a touchscreen display and/or a secondary screen that can display any number of surgical hub 206 tracked data feeds to provide a status. The secondary display may display force to fire (FTF), tissue gap, power level, impedance, tissue compression stability (creep), etc., while the primary display may display only key variables to keep the feed free of clutter. The interactive display may be used to move the display of specific information to the primary display to a desired location, size, color, etc. In the illustrated example, the secondary display may display the instrument proximity displays 6210 on the left side of the display 6200. The local instrument display 6204 on the bottom right side of the display 6200. The local instrument display 6204 presented on the surgical hub display 6200 may display an icon of the end effector 6218, such as the icon of a staple cartridge 6224 currently in use, the size 6226 of the staple cartridge 6224 (e.g., 60 mm), and an icon of the current position of the knife 6228 of the end effector.

A secondary display may be the display 237 as shown in FIG. 5. Referring to FIG. 5, the display 237 located on the instrument 235 can display the wireless or wired attachment of the instrument 235 to the surgical hub 206 and the instrument's communication and/or recording on the surgical hub 206. A setting may be provided on the instrument 235 to enable the user to select mirroring or extending the display to both monitoring devices. The instrument controls may be used to interact with the surgical hub display of the information being sourced on the instrument. The instrument 235 may comprise wireless communication circuits to communicate wirelessly with the surgical hub 206, as described herein.

A first instrument coupled to the surgical hub 206 can pair to a screen of a second instrument coupled to the surgical hub 206 allowing both instruments to display some hybrid combination of information from the two devices of both becoming mirrors of portions of the primary display. The primary display 6200 of the surgical hub 206 can provide a 360° composite top visual view of the surgical site 6208 to avoid collateral structures. For example, a secondary display of the end effector surgical stapler may be provided within the primary display 6200 of the surgical hub 206 or on another display in order to provide better perspective around the areas within a current the field of view 6206.

Figure 17:
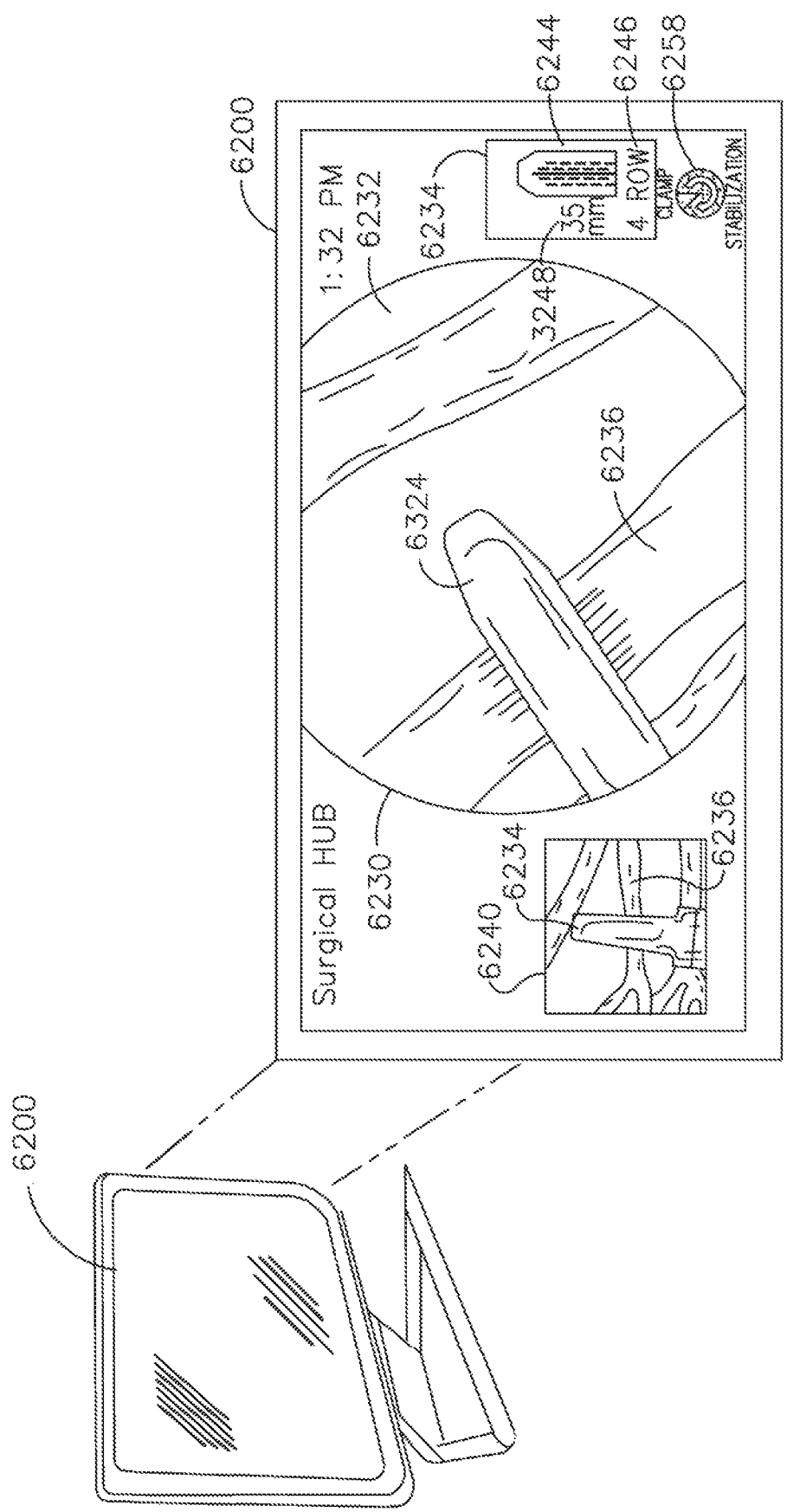
FIG. 17 illustrates an example a primary display of the surgical hub.

FIG. 17 illustrate an example primary display having a composite overhead views of an end-effector 6234 portion of a surgical stapler mapped using two or more imaging arrays or one array and time to provide multiple perspective views of the end-effector 6234 to enable the composite imaging of an overhead field of view. The techniques described herein may be applied to ultrasonic instruments, electrosurgical instruments, combination ultrasonic/electrosurgical instruments, and/or combination surgical stapler/electrosurgical instruments. Several techniques may be performed for overlaying or augmenting images and/or text from multiple image/text sources to present composite images on a display (e.g., a single display).

As shown in FIG. 17, a primary display 6200 of the surgical hub 206 may display a primary window 6230. The primary window 6230 may be located at the center of the screen shows a magnified or exploded narrow angle view of a surgical field of view 6232. The primary window 6230 located in the center of the screen shows a magnified or narrow angle view of an end-effector 6234 of the surgical stapler grasping a vessel 6236. The primary window 6230 may display knitted images to produce a composite image that enables visualization of structures adjacent to the surgical field of view 6232. A second window 6240 may be shown in the lower left corner of the primary display 6200. The second window 6240 displays a knitted image in a wide-angle view at standard focus of the image shown in the primary window 6230 in an overhead view. The overhead view provided in the second window 6240 can enable the viewer to easily see items that are out of the narrow field surgical field of view 6232 without moving the laparoscope, or other imaging device 239 coupled to the imaging module 238 of the surgical hub 206. A third window 6242 can be shown in the lower right corner of the primary display 6200 shows an icon 6244 representative of the staple cartridge of the end-effector 6234 (e.g., a staple cartridge in this instance) and additional information such as "4 Row" indicating the number of staple rows 6246 and "35 mm" indicating the distance 3248 traversed by the knife along the length of the staple cartridge. Below the third window 6242 is displayed an icon 6258 of a frame of the current state of a clamp stabilization sequence that indicates clamp stabilization.

The local display/secondary display may be or may include an augmented reality (AR device). The AR device may include a head-mounted display (HMD). An HMD may include a processor, a non-transitory computer readable memory storage medium, and executable instructions contained within the storage medium that are executable by the processor to carry out methods or portions of methods disclosed herein. The HMD may include a graphics processor for rendering 2D or 3D video and/imaging for display.

Figure 18:
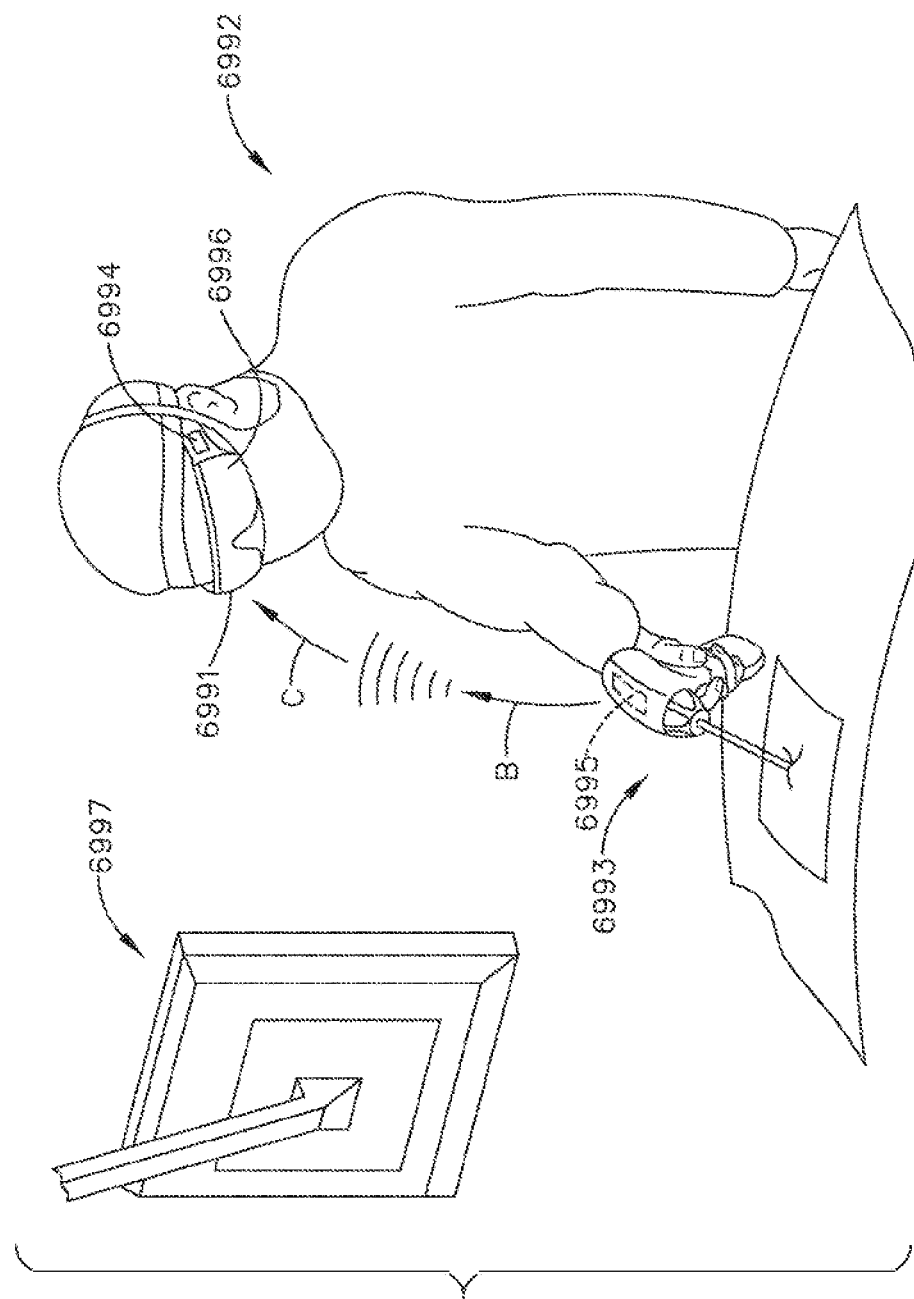
FIG. 18 depicts a perspective view of a surgeon using a surgical instrument that includes a handle assembly housing and a wireless circuit board during a surgical procedure, with the surgeon wearing a set of safety glasses.

FIG. 18 depicts a perspective view of a surgeon using a surgical instrument that includes a handle assembly housing and a wireless circuit board during a surgical procedure, with the surgeon wearing a set of safety glasses. The safety glasses may be or may include an AR device that may serve as a secondary display. The wireless circuit board transmits a signal to a set of safety glasses worn by a surgeon using the surgical instrument during a procedure. The signal is received by a wireless port on the safety glasses. One or more lighting devices on a front lens of the safety glasses change color, fade, or glow in response to the received signal to indicate information to the surgeon about the status of the surgical instrument. The lighting devices are disposable on peripheral edges of the front lens to not distract the direct line of vision of the surgeon. Further examples are disclosed in U.S. Pat. No. 9,011,427, titled SURGICAL INSTRUMENT WITH SAFETY GLASSES, which issued on Apr. 21, 2015, which is herein incorporated by reference in its entirety.

FIG. 18 shows a version of safety glasses 6991 that may be worn by a surgeon 6992 during a surgical procedure while using a medical device. In use, a wireless communications board housed in a surgical instrument 6993 may communicate with a wireless port 6994 on safety glasses 6991. Exemplary surgical instrument 6993 is a battery-operated device, though instrument 6993 could be powered by a cable or otherwise. Instrument 6993 includes an end effector. Particularly, wireless communications board 6995 transmits one or more wireless signals indicated by arrows (B, C) to wireless port 6994 of safety glasses 6991. Safety glasses 6991 receive the signal, analyze the received signal, and display indicated status information received by the signal on lenses 6996 to a user, such as surgeon 6992, wearing safety glasses 6991. Additionally, or alternatively, wireless communications board 6995 transmits a wireless signal to surgical monitor 6997 such that surgical monitor 6997 may display received indicated status information to surgeon 6992, as described above.

A version of the safety glasses 6991 may include lighting device on peripheral edges of the safety glasses 6991. A lighting device provides peripheral-vision sensory feedback of instrument 6993, with which the safety glasses 6991 communicate to a user wearing the safety glasses 6991. The lighting device may be, for example, a light-emitted diode ("LED"), a series of LEDs, or any other suitable lighting device known to those of ordinary skill in the art and apparent in view of the teachings herein.

Referring back to FIG. 19, at 18210, one or more multi-display control parameter(s) may be obtained. At 18215, a current multi-display control mode may be identified based on the multi-display control parameter(s).

For example, the current multi-display control mode may be selected from multiple multi-display control modes that may be preconfigured, dynamically updated, semi-dynamically updated, periodically updated, or preset. The multi-display control modes may support or disable various multi-display control capabilities as described herein.

The multi-display control parameter(s) may include, but not limited to, systems capabilities such as hardware capability, firmware capability and/or software capability associated with the surgical device(s) and/or systems. For example, if secondary display lacks the hardware capability to receive a user indication, the surgical hub may switch to a multi-display control mode that may disable controlling the display content of a primary display via the secondary display.

The multi-display control parameter(s) may include a consumer-controlled parameter, such as a subscription level. For example, a medical facility may purchase a subscription to multi-display control capabilities. Some subscription level(s) may provide the display(s) (e.g., via the hub and/or surgical instrument(s)) access to surgical data gathered from external systems, while others may limit the display control and connectivity to internal devices.

The multi-display control parameter(s) may include available data bandwidth, power capacity and usage, processor and memory utilization, and/or internal or attached systems.

Figure 22:
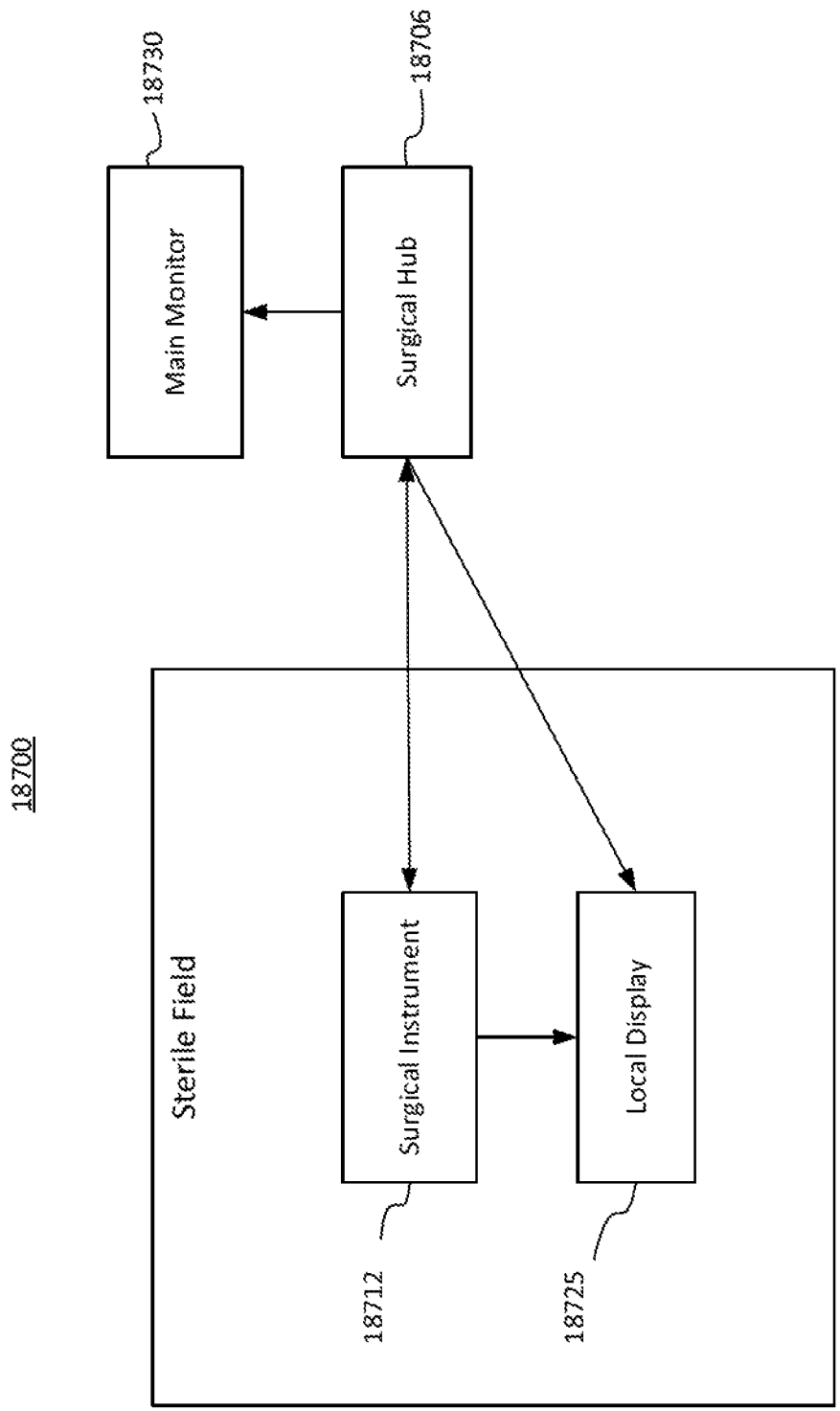
FIG. 22 shows an example multi-display control mode such as a one-way communication mode.
Figure 23:
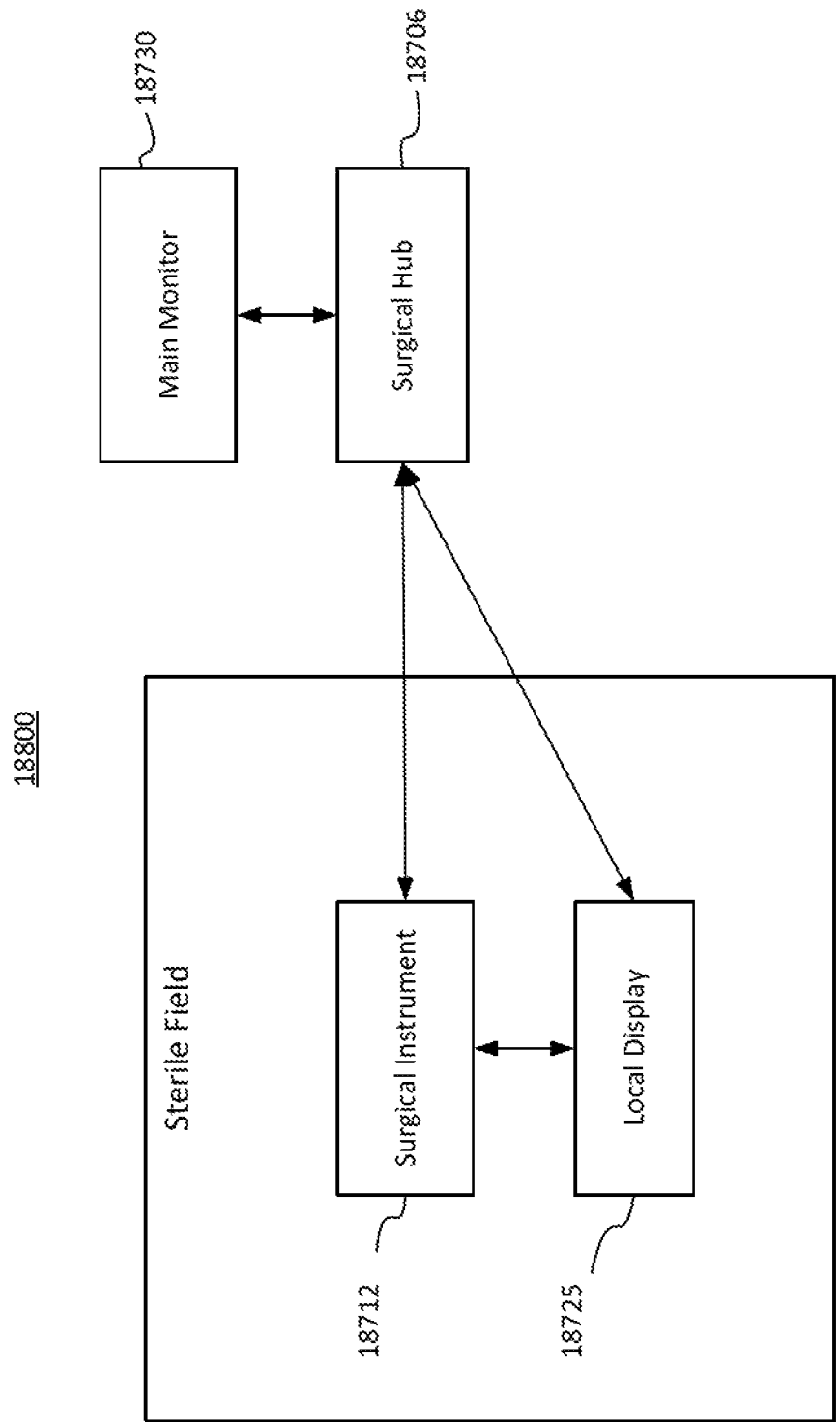
FIG. 23 shows an example multi-display control mode that may support sterile field display-based control.
Figure 24:
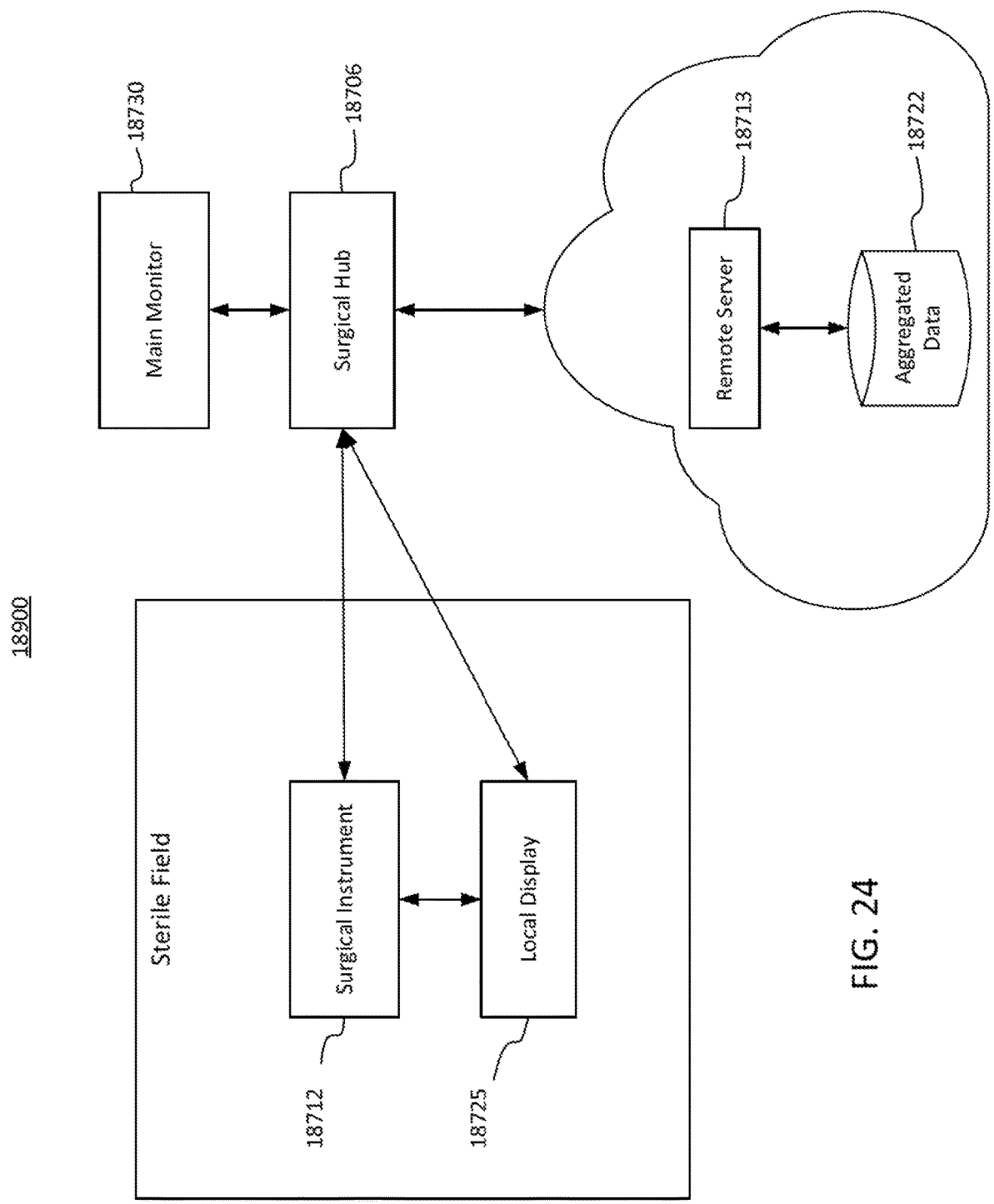
FIG. 24 shows an example multi-display control mode that may support remote data aggregation analysis.

In examples, the multi-display control parameter be or may include an indication from the surgical hub. The multi-display control parameter(s) may include an indication from a tiered system. With reference to FIGS. 22-24, the tiered system may scale the display connectivity and control communication among the surgical hub 18706, the local display 18725, the main display 18730, the communication between the surgical hub 18706 and external server(s) 18713/18722 and/or the like, based on the available data bandwidth, power capacity and usage, processor and memory utilization, and/or internal or attached systems. The tiered system may determine max communication capabilities the surgical system may operate under.

For example, upon detecting the power capability associated with the operation room, associated with the surgical hub, and/or associated with a medical facility is below a threshold, the tiered system may scale down the multi-display control capabilities. For example, upon detecting available data bandwidth is below a threshold, memory utilization is above a certain threshold, power usage is above a certain threshold, and/or other system conditions that may warrant scaling down the multi-display control capabilities, the tiered system may limit or disable the interactions between the primary and secondary display(s), the surgical hub and the display(s) and/or the communication between the surgical system (such as the surgical hub and/or the surgical instruments in the OR) and external server(s). For example, sterile field display-based control mode 18800 (as shown in FIG. 23) may be scaled down to one-way communication mode 18700 (as shown in FIG. 22). External communication capabilities (as described herein with reference to FIG. 24) may be disabled. In examples, the tiered system may be a module within the surgical hub or may be a system external to the surgical hub.

At 18220, whether to generate visualization control data associated with the display outside of the surgical sterile field may be determined based on the current multi-display control mode. At 18230, the device may interact with the display inside the surgical sterile field and the display outside of the surgical sterile field based on the determination.

The surgical system may operate under various multi-display control modes such as one-way communication mode, sterile field display-based control mode, and/or remote aggregation analysis mode.

FIG. 22 shows an example multi-display control mode such as a one-way communication mode 18700. As shown, surgical instrument 18712 and local display 18725 may be placed in the sterile field. The local display 18725 may be part of the surgical instrument 18712 or may be external to the surgical instrument 18712. Main monitor 18730 may be a primary display as described herein and may be located outside of the sterile field. The surgical hub 18706 may be located outside of the sterile field, as shown. In some examples, the surgical hub 18706 may be located inside the sterile field. The local display 18725 can receive information from the surgical instrument 18712 for display, and/or receive information from the surgical hub 18706 for display. The information from the surgical instrument 18712 and the information from the surgical hub 18706 may be combined for display at the local display 18725. The local display 18725 may provide a place the surgeon can view or access a part of the overall data environment.

As shown in FIG. 22, the surgical instrument 18712 may receive, from the surgical hub 18706, content for displaying on the local display 18725 inside the surgical sterile field and send the received content to the display 18725. In some examples, the local display 18725 may receive display content from the surgical hub 18706. The surgical hub 18706 may send display content to the main monitor 18730. In the example one-way communication mode 18700, generation of the visualization control data associated with the display outside of the surgical sterile field based on indication(s) received via the local display 18725 may be disabled. Generation of aggregation analysis requests may be disabled.

FIG. 23 shows an example multi-display control mode 18800 that may support sterile field display-based control. As shown, surgical instrument 18712 and local display 18725 may be placed in the sterile field. The local display 18725 may be part of the surgical instrument 18712 or may be external to the surgical instrument 18712. Main monitor 18730 may be a primary display as described herein and may be located outside of the sterile field. In some examples, the main display may be or may include display(s) outside the sterile field, such as the display 107 or 109 as shown in FIG. 2. In some examples, the main display may be or may include a display inside the sterile field, such as the primary display 119 as shown in FIG. 2. The surgical hub 18706 may be located outside of the sterile field, as shown. In some examples, the surgical hub 18706 may be located inside the sterile field. As shown in FIG. 23, the surgical instrument 18712 may receive, from the surgical hub 18706, content for displaying on the local display 18725 inside the surgical sterile field and send the received content to the display 18725. In some examples, the local display 18725 may receive display content from the surgical hub 18706. The surgical hub 18706 may send display content to the main monitor 18730.

As shown in FIG. 23, the surgical instrument 18712 may receive the visualization control data for controlling the main display 18730 from the local display 18725 inside the surgical sterile field. The surgical instrument 18712 may send the visualization control data for controlling the main display 18730 to the main display 18730. The surgical instrument 18712 may send he visualization control data directly to the main display 18730. The surgical instrument 18712 may send he visualization control data via the surgical hub 18706. The main display 18730 may adjust its display in accordance with the visualization control data.

In some examples, the surgical hub 18706 may receive the visualization control data for controlling the main display 18730 from the local display 18725 inside the surgical sterile field. The surgical hub 18706 may send the visualization control data for controlling the main display 18730 to the main display 18730. The main display 18730 may adjust its display based on the visualization control data.

For example, a secondary display such as the local display 18725 shown in FIG. 23 may serve as a user interface for displaying and controlling of surgical hub functions from within the sterile field. The secondary display could be used to change display locations, what information is displayed where, and/or pass off control of specific functions or devices.

During a surgical procedure, the surgeon may not have a user interface device accessible for interactive input by the surgeon and display within the sterile field. Thus, the surgeon may not interface with the user interface device and the surgical hub from within the sterile field and cannot control other surgical devices through the surgical hub from within the sterile field.

The local display 18725 may include a display unit that may be used within the sterile field and accessible for input and display by the surgeon to allow the surgeon to have interactive input control from the sterile field to control other surgical devices and/or displays coupled to the surgical hub. The display unit may be sterile and located within the sterile field to allow the surgeons to interface with the display unit and the surgical hub to directly interface and configure instruments as necessary without leaving the sterile field. The display unit may be a master device and may be used for display, control, interchanges of tool control, allowing feeds from other surgical hubs without the surgeon leaving the sterile field.

The display unit may be or may include an interactive touchscreen display, an interface configured to couple the interactive touchscreen display to a surgical hub, a processor, and a memory coupled to the processor. The memory may store instructions executable by the processor to receive input commands from the interactive touchscreen display located inside a sterile field and may transmit the input commands to a surgical hub to control devices coupled to the surgical hub located outside the sterile field.

The local display 18725 inside the surgical sterile field may be a secondary surgeon display within the sterile field and accessible for input and display by the surgeon within the sterile field interactive control displays. Sterile field interactive control displays may be shared or dedicated to a particular healthcare professional.

The local display 18725 may be mounted on the operating table, on a stand, or laying on the abdomen or chest of the patient. The sterile field display 18725 is sterile and allows the surgeons to interface with the non-sterile field display 18730 and the surgical hub 18706 via the sterile field display 18725. This may provide the surgeons control of the system and may allow them to directly interface and configure the non-sterile field display(s) 18730 as necessary (e.g., without leaving the sterile field). The sterile field display 18725 may be configured as a master device and may be used for display, control, interchanges of tool control, allowing feeds from other surgical hubs (e.g., without the surgeon leaving the sterile field).

A surgical instrument such as the surgical instrument 18712 may include the local display 18725. The surgical instrument 18712 may include an interactive touchscreen display, an interface configured to couple the interactive touchscreen display to a surgical hub, and a control circuit configured to receive input commands from the interactive touchscreen display located inside a sterile field and transmit the input commands to a surgical hub to control devices coupled to the surgical hub located outside the sterile field.

A non-transitory computer readable medium may store computer readable instructions which, when executed, may cause a machine to receive input commands from an interactive touchscreen display located inside a sterile field and transmit the input commands to a surgical hub through an interface configured to couple the interactive touchscreen display to the surgical hub, to control displays coupled to the surgical hub located outside the sterile field.

Providing the display unit designed to be used within the sterile field and accessible for input and display by the surgeon provides the surgeon interactive input control from the sterile field to control other surgical display(s) coupled to the surgical hub.

A secondary user interface via the display unit may enable control of non-sterile display(s) from within a sterile field. The display unit may include a display device such as an i-pad, e.g., a portable interactive touchscreen display device configured to be introduced into the operating theater in a sterile manner. It could be paired like any other device or it could be location sensitive. The display device may be allowed to function in this manner whenever the display device is placed over a specific location of the draped abdomen of the patient during a surgical procedure.

The local display 18725 inside the surgical sterile field may generate the visualization control data for controlling a non-sterile display such as the main display 18730 outside the surgical sterile field. For example, the visualization control data may indicate a change of display location and/or what information and where the information may be displayed. The visualization control data may indicate passing off the control of specific functions or devices.

For example, the local display 18725 may be re-configure the wireless activation devices within the operating theater and their paired energy device if a surgeon hands the device to another. The local display 18725 may be employed as an interactable scalable secondary display allowing the surgeon to overlay other feeds or images like laser Doppler scanning arrays. The local display 18725 may be employed to call up a pre-operative scan or image to review. Once vessel path and depth and device trajectory are estimated, the surgeon may use a sterile field interactable scalable secondary display to overlay other feeds or images. Examples of sterile field display-based control are described under heading "Surgical Hub with Direct Interface Control with Secondary Surgeon Display Units Designed to be within the Sterile Field and Accessible for Input and Display by the Surgeon" in U.S. patent application Ser. No. 15/940,671, titled SURGICAL HUB SPATIAL AWARENESS TO DETERMINE DEVICES IN OPERATING THEATER, which was filed on Mar. 29, 2018, which is herein incorporated by reference in its entirety.

FIG. 24 shows an example multi-display control mode 18900 that may support remote data aggregation analysis. As shown, the surgical instrument 18712 may receive the visualization control data for controlling the main display 18730 from the local display 18725 inside the surgical sterile field. The surgical instrument 18712 may send the visualization control data for controlling the main display 18730 to the main display 18730 (e.g., directly, or via the surgical hub 18706). The main display 18730 may adjust its display based on the visualization control data. In some examples, the surgical hub 18706 may receive the visualization control data for controlling the main display 18730 from the local display 18725 inside the surgical sterile field. The surgical hub 18706 may send the visualization control data for controlling the main display 18730 to the main display 18730. The main display 18730 may adjust its display based on the visualization control data.

As shown in FIG. 24, the local display 18725 may communicate with a remote server 18713 and/or aggregated database 18722 through the surgical hub 18706. The local display 18725 may access and display of data and/or analyses residing on the remote server 18713. The local display 18725 may combine the data and/or analyses retrieved from the remote server 18713 with locally created content and data for display.

FIG. 20 shows an example flow 18300 for operating under tiered multi-display control mode(s). As shown in FIG. 20, at 18312, the current multi-display control mode may be identified based on the multi-display control parameter. At 18315, whether the current multi-display control mode supports sterile field display-based control may be determined. Upon determining that the current multi-display control mode supports sterile field display-based control, at 18316, visualization control data associated with the display outside of the surgical sterile field may be obtained. The visualization control data may be obtained via a display inside a surgical sterile field as described herein. Upon determining that the current multi-display control mode does not support sterile field display-based control, at 18318, generation of the visualization control data associated with a display outside of the surgical sterile field may be disabled.

Figure 21:
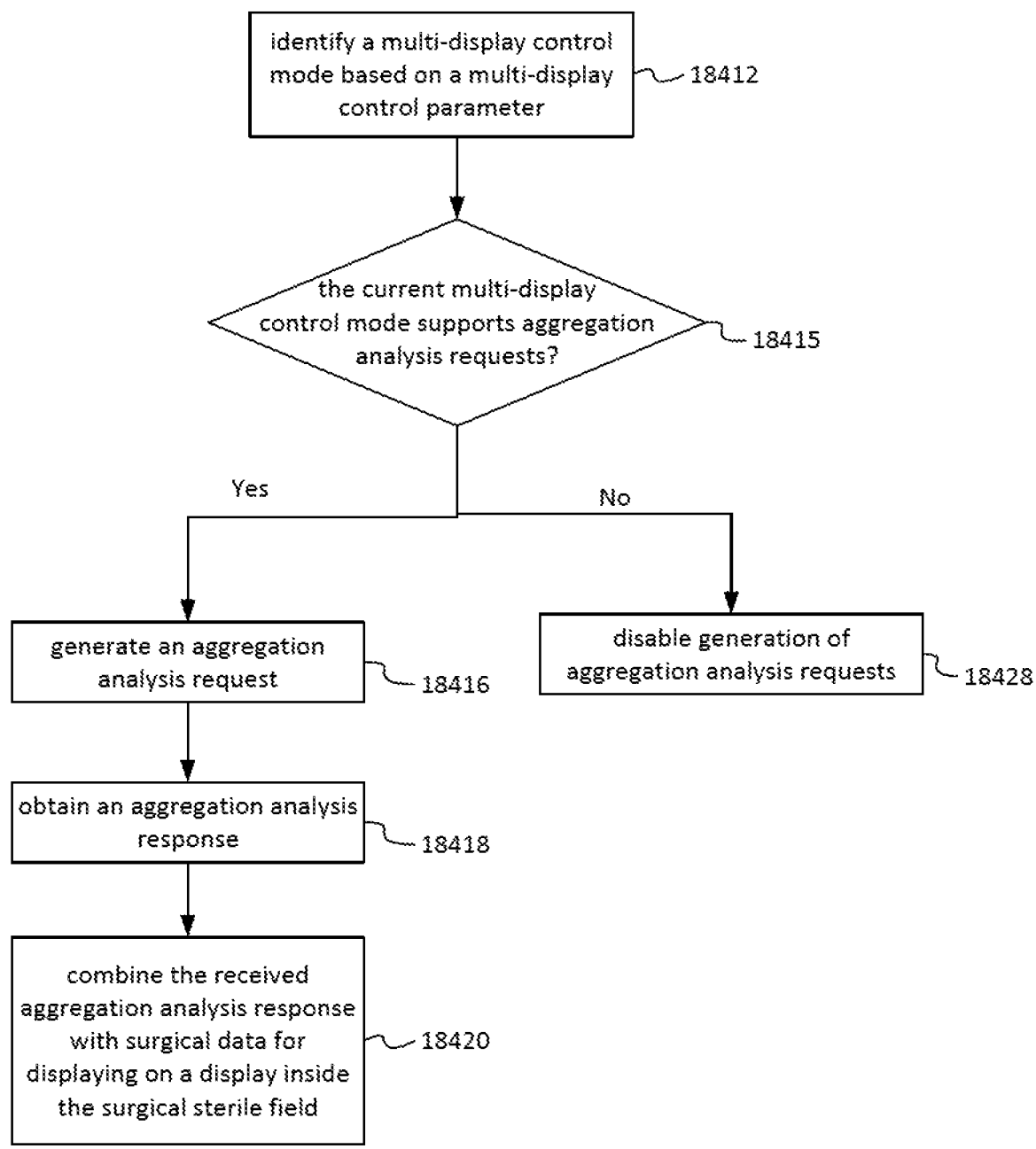
FIG. 21 shows an example flow for operating under tiered multi-display control mode(s).

FIG. 21 shows an example flow 18400 for operating under tiered multi-display control mode(s). As shown in FIG. 21, at 18412, the current multi-display control mode may be identified based on the one or more multi-display control parameter(s). At 18415, whether the current multi-display control mode supports aggregation analysis requests may be determined based on the current multi-display control mode. Based on a determination that the current multi-display control mode supports aggregation analysis requests, an aggregation analysis request may be generated at 18416.

For example, the aggregation analysis request may include a request for historic datasets, steps-for-use, issue resolution, images associated with the current procedure, videos associated with the current procedure, comparative information from prior patients that present in a similar fashion, and/or procedural suggestions.

An aggregation analysis response may be obtained at 18418 and combined with surgical data generated based on the sensed surgical data for displaying on the display inside the surgical sterile field at 18420. At 18428, based on a determination that the current multi-display control mode does not support aggregation analysis requests, generation of aggregation analysis requests may be disabled.

Examples of aggregation (e.g., remote aggregation), requests and analysis are described in detail in U.S. patent application Ser. No. 15/940,668 titled AGGREGATION AND REPORTING OF SURGICAL HUB DATA; filed on Mar. 29, 2018, which is herein incorporated by reference in its entirety.

Figure 25:
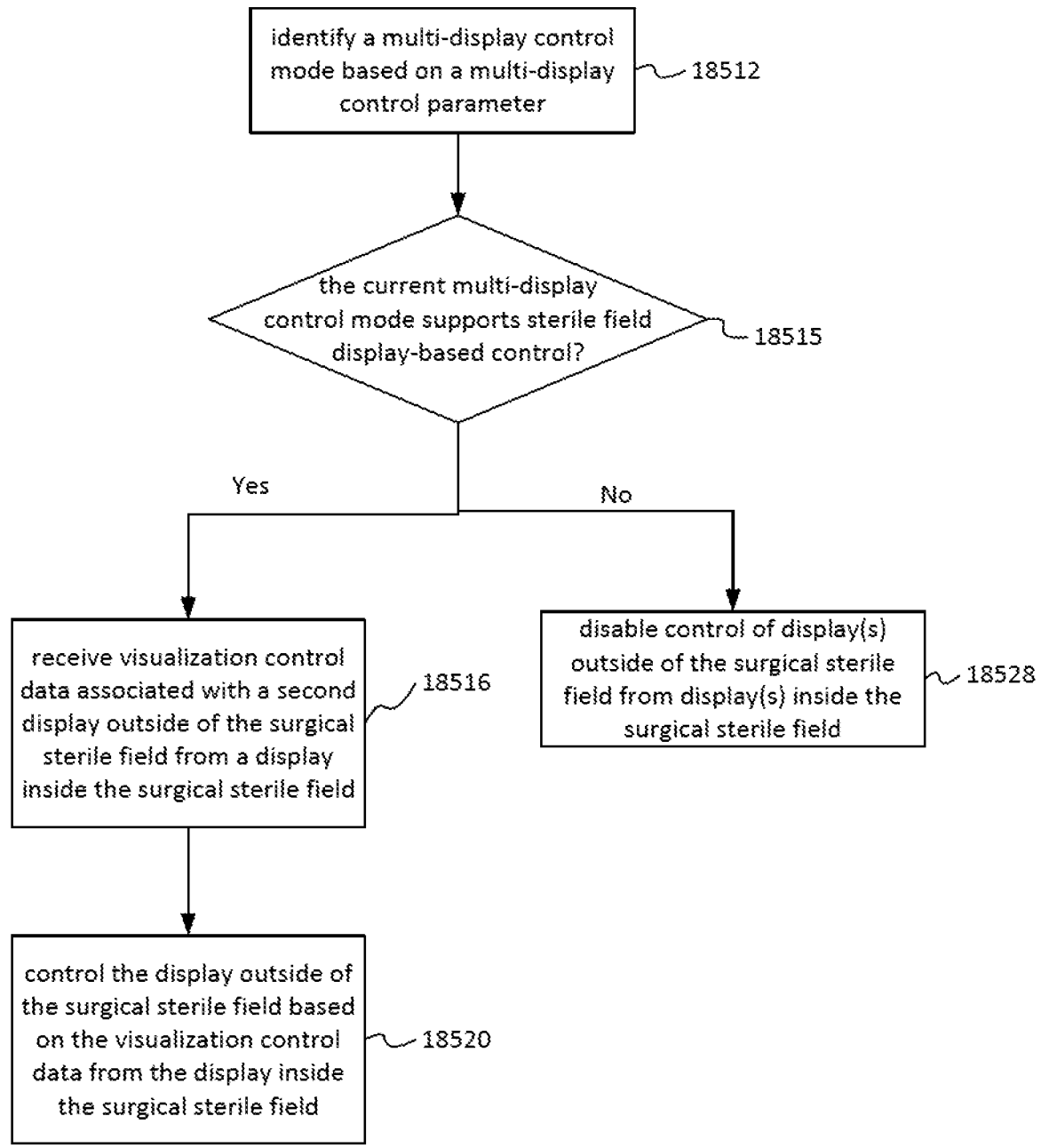
FIG. 25 shows an example flow for operating under tiered multi-display control mode(s).

FIG. 25 shows an example flow 18500 for operating under tiered multi-display control mode(s). In examples, the steps shown in FIG. 25 may be performed by a surgical hub as described herein. As shown in FIG. 25, at 18512, the current multi-display control mode may be identified based on one or more multi-display control parameter(s). At 18515, whether the current multi-display control mode supports sterile field display-based control may be determined. Upon determining that the current multi-display control mode supports sterile field display-based control, at 18516, visualization control data associated with one or more display(s) outside of the surgical sterile field may be received from one or more display(s) inside the surgical sterile field. For example, visualization control data generated via the secondary display(s) can control to change, focus, or control that data displayed on the display(s) outside the sterile field. This may allow a healthcare personnel to more seamlessly view data relative to other imaging or even pre-surgery imaging mechanisms.

For example, sterile field display-based control may allow data to move back and forth, to and from, the surgical hub. The display in the sterile field may act as a control system that may control display location of information (such as on a display outside the sterile field), the storage location of information, etc.

At 18520, the display(s) outside of the surgical sterile field may be controlled based on the visualization control data from the display inside the surgical sterile field. Upon determining that the current multi-display control mode does not support sterile field display-based control, at 18528, control of display(s) outside of the surgical sterile field from display(s) inside the surgical sterile field may be disabled. In some examples, steps 18512, 18515, 18516, 18520 and 18528 may be performed by a surgical hub. In some examples, steps 18512, 18515, 18516, 18520 and 18528 may be performed by a surgical instrument.

Figure 26:
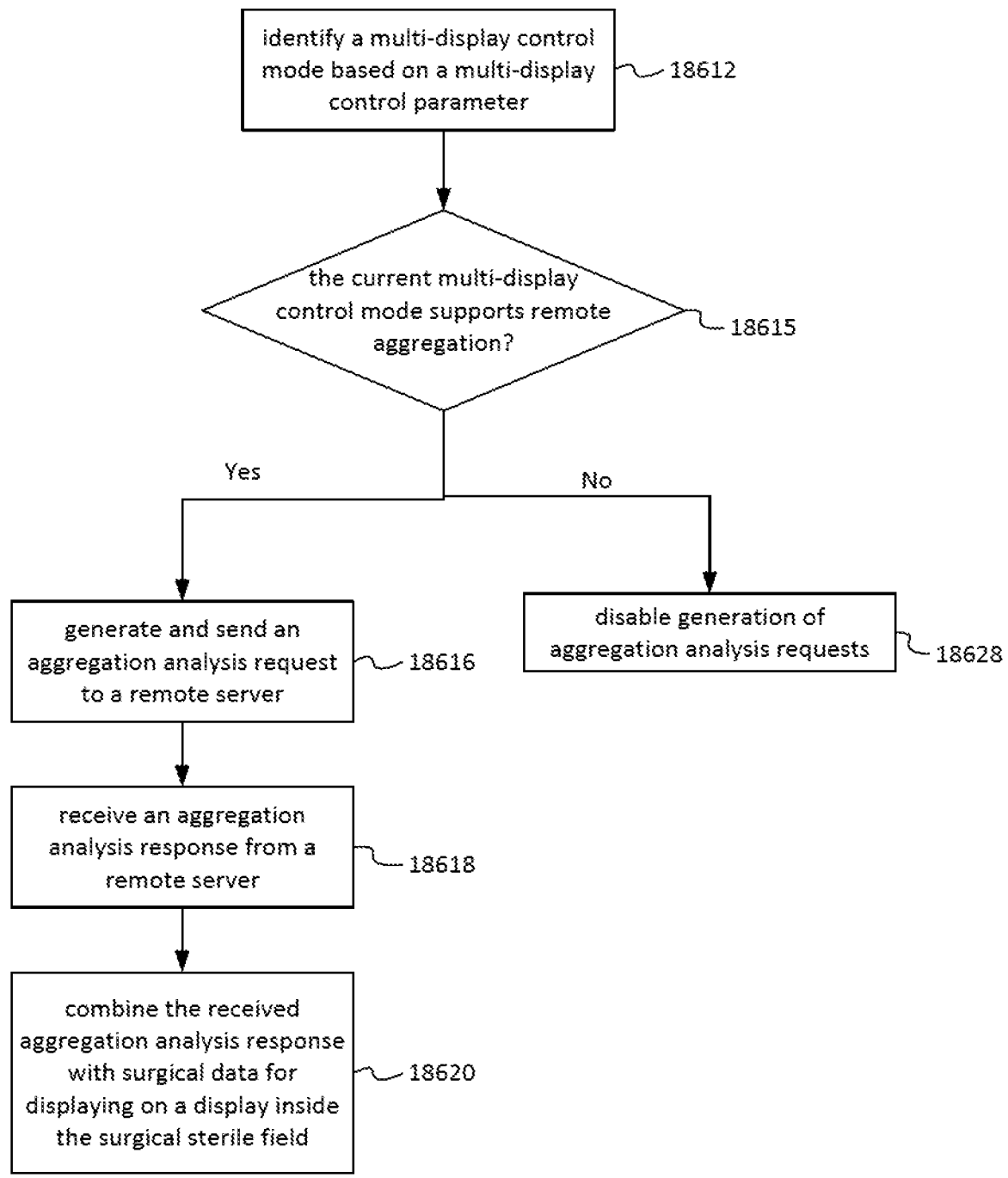
FIG. 26 shows an example flow for operating under tiered multi-display control mode(s).

FIG. 26 shows an example flow 18600 for operating under tiered multi-display control mode(s). In examples, the steps shown in FIG. 25 may be performed by a surgical hub as described herein. As shown in FIG. 26, at 18612, the current multi-display control mode may be identified based on the multi-display control parameter. At 18615, whether the current multi-display control mode supports remote aggregation analysis requests may be determined based on the current multi-display control mode. Based on a determination that the current multi-display control mode supports remote aggregation analysis requests, an aggregation analysis request may be generated and sent to a remote server at 18616.

For example, the aggregation analysis request may include a request for historic datasets, steps-for-use, issue resolution, images associated with the current procedure, videos associated with the current procedure, comparative information from prior patients that present in a similar fashion, and/or procedural suggestions. The aggregation analysis request being generated based on an indication from the display inside the sterile field.

An aggregation analysis response may be received from the remote server at 18618. The aggregation analysis response may correspond to the aggregation analysis request. For example, the aggregation analysis response may include, but not limited torn historic datasets, steps-for-use, issue resolution, images associated with the current procedure, videos associated with the current procedure, comparative information from prior patients that present in a similar fashion, and/or procedural suggestions. As shown, the received aggregation analysis response may be combined with surgical data generated based on the sensed surgical data for displaying on the display inside the surgical sterile field at 18620. At 18628, based on a determination that the current multi-display control mode does not support remote aggregation analysis requests, generation of aggregation analysis requests may be disabled.

In some examples, steps 18612, 18615, 18616, 18618, 18620 and 18628 may be performed by a surgical hub. In some examples, steps 18612, 18615, 18616, 18618, 18620 and 18628 may be performed by a surgical instrument.

The invention claimed is:

1. A powered surgical instrument comprising:
   a communication module operably connected to a first display inside a surgical sterile field and a second display outside of the surgical sterile field; and
   a processor configured to:
   obtain a multi-display control parameter;
   identify a current multi-display control mode based on the multi-display control parameter;
   determine, based on the current multi-display control mode, whether to generate visualization control data configured to control display content on the second display outside of the surgical sterile field in response to a user indication at the first display inside the surgical sterile field; and interact with the first display inside the surgical sterile field and the second display outside of the surgical sterile field based on the determination.

2. The powered surgical instrument of claim 1, wherein the communication module is operably connected to a surgical hub, and the multi-display control parameter comprises an indication from the surgical hub.

3. The powered surgical instrument of claim 1, wherein the communication module is operably connected to a surgical hub, and the processor is further configured to:
receive, from the surgical hub, content for displaying on first display inside the surgical sterile field; and
send the received content to the first display.

4. The powered surgical instrument of claim 1, wherein the processor is further configured to:
based on a determination that the current multi-display control mode supports sterile field display-based control, obtain, via the first display inside the surgical sterile field, the visualization control data associated with the second display outside of the surgical sterile field; and
send the visualization control data associated with the second display to a surgical hub for controlling the second display outside of the surgical sterile field.

5. The powered surgical instrument of claim 1, wherein the processor is further configured to:
based on a determination that the current multi-display control mode does not support sterile field display-based control, disable generation of the visualization control data associated with the second display outside of the surgical sterile field.

6. The powered surgical instrument of claim 1, wherein the communication module is operably connected to a surgical hub, the powered surgical instrument comprises at least one sensor for sensing surgical data, and the processor is further configured to:
determine, based on the current multi-display control mode, whether to request an aggregation analysis from a remote server via the surgical hub;
based on a determination to request the aggregation analysis, generate an aggregation analysis request;
receive an aggregation analysis response via the communication module; and
combine the received aggregation analysis response with surgical data generated based on the sensed surgical data for displaying on the first display inside the surgical sterile field.

7. The powered surgical instrument of claim 1, wherein the powered surgical instrument comprises the first display inside the surgical sterile field.

8. The powered surgical instrument of claim 1, wherein the first display inside the surgical sterile field is external to the powered surgical instrument.

9. The powered surgical instrument of claim 1, wherein the multi-display control parameter comprises at least one of:
available processing capability associated with powered surgical instrument;
available power capability associated with powered surgical instrument; or
available data bandwidth associated with powered surgical instrument.

10. The powered surgical instrument of claim 1, wherein the multi-display control parameter comprises a subscription level associated with multi-display control, and the processor is further configured to:

based on a determination that the subscription level associated with multi-display control supports sterile field display-based control, obtain, via the first display inside the surgical sterile field, the visualization control data configured to control the display content on the second display outside of the surgical sterile field, and send the visualization control data; and
based on a determination that the subscription level associated with multi-display control does not support sterile field display-based control, disable generation of the visualization control data configured to control the display content the second display outside of the surgical sterile field.

11. The powered surgical instrument of claim 1, wherein the processor is further configured to:
based on a determination that the current multi-display control mode supports sterile field display-based control, receive the user indication, the user indication indicating a request of changing the display content on the second display outside of the surgical sterile field;
generate the visualization control data associated with the second display outside of the surgical sterile field based on the received user indication; and
send the visualization control data associated with the second display outside of the surgical sterile field to a surgical hub for controlling the second display outside of the surgical sterile field.

12. The powered surgical instrument of claim 11, wherein the user indication indicating the request of changing the display content on the second display outside of the surgical sterile field is received via the first display inside a surgical sterile field.

13. The powered surgical instrument of claim 11, wherein the user indication indicates at least one of:
projecting content associated with the first display inside the surgical sterile field onto the second display outside of the surgical sterile field, or
removing the content associated with the first display inside the surgical sterile field from the second display outside of the surgical sterile field.

14. A surgical hub comprising:
a communication module operably connected to a surgical instrument, a first display inside a surgical sterile field and a second display outside of the surgical sterile field; and
a processor configured to:
obtain a multi-display control parameter;
identify a current multi-display control mode based on the multi-display control parameter;
determine, based on the current multi-display control mode, whether to receive visualization control data configured to control display content on the second display outside of the surgical sterile field from the first display inside a surgical sterile field in response to a user indication at the first display inside the surgical sterile field; and
interact with the first display inside the surgical sterile field and the second display outside of the surgical sterile field based on the determination.

15. The surgical hub of claim 14, wherein the processor is further configured to:
based on a determination that the current multi-display control mode supports sterile field display-based control, receive the visualization control data associated with the second display outside of the surgical sterile field; and control the second display outside of the surgical sterile field based on the received visualization control data associated with the second display outside of the surgical sterile field.

16. The surgical hub of claim 14, wherein the processor is further configured to:
  determine, based on the current multi-display control mode, whether to retrieve aggregation analysis from a remote server for displaying on the first display inside the surgical sterile field;
  based on a determination that the current multi-display control mode supports remote aggregation, generate an aggregation analysis request;
  receive an aggregation analysis response via the communication module; and
  combine the received aggregation analysis response with surgical data received from the surgical instrument to generate content for displaying on first display inside the surgical sterile field.

17. A method for communicating with a first display inside a surgical sterile field and a second display outside of the surgical sterile field, the method comprising:
  obtaining a multi-display control parameter;
  identifying a current multi-display control mode based on the multi-display control parameter;
  determining, based on the current multi-display control mode, whether to generate visualization control data configured to control display content on the second display outside of the surgical sterile field in response to a user indication at the first display inside the surgical sterile field; and
  interacting with the first display inside the surgical sterile field and the second display outside of the surgical sterile field based on the determination.

18. The method of claim 17, further comprising:
  determining, based on the current multi-display control mode, whether to request an aggregation analysis from a remote server;
  based on a determination to request the aggregation analysis, generating an aggregation analysis request;
  receiving an aggregation analysis response;
  receiving sensed surgical data from at least one sensor; and
  combining the received aggregation analysis response with surgical data generated based on the sensed surgical data for displaying on the first display inside the surgical sterile field.

19. The method of claim 17, further comprising:
  based on a determination that the current multi-display control mode supports sterile field display-based control, receiving the user indication, the user indication indicating a request of changing the display content on the second display outside of the surgical sterile field;
  generating the visualization control data associated with the second display outside of the surgical sterile field based on the received user indication; and
  sending the visualization control data associated with the second display outside of the surgical sterile field for controlling the second display outside of the surgical sterile field.

20. The method of claim 19, wherein the user indication indicating the request of changing the display content on the second display outside of the surgical sterile field is received via the first display inside a surgical sterile field.

* * * * *